United States Patent [19]

Marescaux et al.

[11] Patent Number: 5,229,379
[45] Date of Patent: Jul. 20, 1993

[54] CERTAIN N-SUBSTITUTED-AMINO-ALKANE PHOSPHINIC ACID DERIVATIVES HAVING ANTI-EPILEPTIC PROPERTIES

[75] Inventors: Christian Marescaux, Strasbourg, France; Raymond Bernasconi, Oberwil, Switzerland; Markus Schmutz, Schönenbuch, Switzerland; Wolfgang Fröstl, Basel, Switzerland; Stuart J. Mickel, Lausen, Switzerland

[73] Assignee: Ciba-Geigy Corporation, Ardsley, N.Y.

[21] Appl. No.: 718,503

[22] Filed: Jun. 20, 1991

[30] Foreign Application Priority Data

Jun. 22, 1990 [CH] Switzerland ............ 2092/90
Feb. 13, 1991 [CH] Switzerland ............ 440/91
Apr. 22, 1991 [CH] Switzerland ............ 1199/91

[51] Int. Cl.$^5$ .................. A61K 31/66; C07F 9/38; C07F 9/30; C07F 9/58
[52] U.S. Cl. .................. 514/114; 558/166; 562/11; 546/89; 514/89
[58] Field of Search .................. 562/11; 558/166; 514/114

[56] References Cited

U.S. PATENT DOCUMENTS

| | | | |
|---|---|---|---|
| 2,535,175 | 5/1949 | Tawney | 558/87 |
| 3,184,496 | 5/1965 | Baranavckas | 559/119 |
| 3,374,288 | 3/1968 | Lange | 525/408 |
| 3,385,822 | 3/1968 | Brown | 528/30 |
| 3,493,639 | 2/1970 | Tavs | 558/125 |
| 3,637,763 | 1/1972 | Firestone | 549/217 |
| 3,784,590 | 1/1974 | Firestone | 558/175 |
| 3,812,221 | 5/1974 | Braden | 558/145 |
| 3,970,586 | 7/1976 | Schliebs | 252/355 |
| 4,064,163 | 12/1977 | Drach | 562/25 |
| 4,322,375 | 3/1982 | Maier | 558/193 |
| 4,390,690 | 6/1983 | DiGiacamo | 528/395 |
| 4,399,287 | 8/1983 | Baillie | 548/119 |
| 4,466,913 | 8/1984 | Tsuruoka | 562/15 |
| 4,536,355 | 8/1985 | Lee | 558/169 |
| 4,618,358 | 10/1986 | Maier | 71/86 |
| 4,656,298 | 4/1987 | Dingwall | 556/12 |
| 4,657,899 | 4/1987 | Rzeszotarski | 562/11 |
| 4,740,322 | 4/1988 | Thottathil | 562/8 |
| 4,772,738 | 9/1988 | Dingwall | 558/175 |
| 4,908,465 | 3/1990 | Dingwall | 558/175 |
| 5,004,826 | 4/1991 | Dingwall | 558/169 |
| 5,013,863 | 5/1991 | Baylis | 562/11 |
| 5,051,524 | 9/1991 | Baylis | 558/145 |

FOREIGN PATENT DOCUMENTS

| | | | |
|---|---|---|---|
| 009348 | 4/1980 | European Pat. Off. | 562/10 |
| 0068497 | 1/1983 | European Pat. Off. | 562/8 |
| 0093081 | 11/1983 | European Pat. Off. | 558/169 |
| 0181833 | 5/1986 | European Pat. Off. | 562/8 |
| 0319479 | 6/1989 | European Pat. Off. | 562/11 |
| 1525262 | 8/1974 | United Kingdom | 562/12 |
| 1351503 | 7/1990 | United Kingdom | 558/166 |

OTHER PUBLICATIONS

Neurology 41 (Supp. 1) 151, Abs. 1315 (1991).
Aust. J. Chem. 33, 292 (1980).
Br. J. Pharm. 101, 949.
Chem. Abs. 57, 5946 (1962).
Chem. Abs. 97, 92585v (1982).
J. Med. Chem. 27, 654 (1984).
J. Pharma and Experimental Ther. 235(1) (1985).

Primary Examiner—Alan L. Rotman
Attorney, Agent, or Firm—Irving M. Fishman; Karen G. Kaiser; Barbara J. Ikeler

[57] ABSTRACT

Compounds having GABA$_B$-antagonistic properties, for example those of formula I

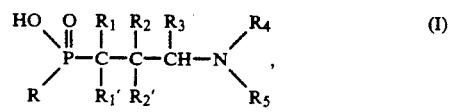

wherein one of the radicals $R_1$, $R_2$ and $R_3$ is hydrogen or an aliphatic, cycloaliphatic, araliphatic or aromatic radical, another is hydrogen or, in the case of $R_1$ or $R_2$, hydroxy or, in the case of $R_1$, halogen or, in the case of $R_2$ together with $R_2'$, oxo, and the remaining radical is hydrogen, $R_1'$ is hydrogen or halogen, $R_2'$ is hydrogen, hydroxy or, together with $R_2$, is oxo, $R_4$ and $R_5$ are hydrogen or $R_4$ is an araliphatic or heteroarylaliphatic radical and $R_5$ is hydrogen or an aliphatic radical, and R is an aliphatic, cycloaliphatic, cycloaliphatic-aliphatic, araliphatic, heteroarylaliphatic or aromatic radical having at least 2 carbon atoms or, when $R_1$ is hydrogen or hydroxy, $R_2$ is an aromatic radical and $R_1'$, $R_2'$ and $R_3$ are hydrogen, R is methyl, and their pharmaceutically acceptable salts, can be used as active ingredients in medicaments for the treatment of epilepsies of the "petit mal" type. The invention relates also to novel compounds of formula I and processes for the preparation thereof.

20 Claims, No Drawings

CERTAIN N-SUBSTITUTED-AMINO-ALKANE PHOSPHINIC ACID DERIVATIVES HAVING ANTI-EPILEPTIC PROPERTIES

The invention relates to the use of compounds having $GABA_B$-antagonistic properties as anti-epileptics for the treatment of epilepsies of the "petit mal" type and for suppressing "petit mal"-type conditions which may arise in the case of treatment with known anti-epileptics, and for the preparation of an anti-epileptic for the treatment of epilepsies of the "petit mal" type, to anti-epileptic medicaments comprising those compounds and a process for the preparation of such medicaments, and to a method, characterised by the administration of such a medicament, of treating epileptic disorders of the "petit mal" type and of suppressing "petit mal"-type conditions which may arise in the case of treatment with known anti-epileptics, and also to novel compounds having $GABA_B$-antagonistic properties, to processes for the preparation thereof and to pharmaceutical compositions comprising them.

Compounds having $GABA_B$-antagonistic properties are to be understood as being compounds that are able to bind to $GABA_B$-receptors and act on them as antogonists of GABA ($\gamma$-aminobutyric acid). They are, for example, compounds of formula I

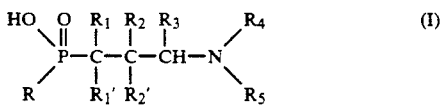

wherein one of the radicals $R_1$, $R_2$ and $R_3$ is hydrogen or an aliphatic, cycloaliphatic, araliphatic or aromatic radical, another is hydrogen or, in the case of $R_1$ or $R_2$, hydroxy or, in the case of $R_1$, halogen or, in the case of $R_2$ together with $R_2'$, oxo, and the remaining radical is hydrogen, $R_1'$ is hydrogen or halogen, $R_2'$ is hydrogen, hydroxy or, together with $R_2$, is oxo, $R_4$ and $R_5$ are hydrogen or $R_4$ is an araliphatic or heteroarylaliphatic radical and $R_5$ is hydrogen, an aliphatic radical or a group $R_4$, and R is an aliphatic, cycloaliphatic, cycloaliphatic-aliphatic, araliphatic, heteroarylaliphatic or aromatic radical having at least 2 carbon atoms or, when $R_1$ is hydrogen or hydroxy, $R_2$ is an aromatic radical and $R_1'$, $R_2'$ and $R_3$ are hydrogen, R is methyl, and their pharmaceutically acceptable salts.

Novel compounds having $GABA_B$-antagonistic properties are especially araliphatically N-substituted aminoalkanephosphinic acids of formula I wherein $R_1$, $R_1'$, $R_2'$ and $R_3$ are hydrogen, $R_2$ is hydrogen or hydroxy, $R_4$ is an araliphatic radical other than unsubstituted 1-phenyl-lower alkyl, or is a heteroarylaliphatic radical, $R_5$ is hydrogen, lower alkyl or a group $R_4$, and R is an aliphatic, cycloaliphatic, cycloaliphatic-aliphatic or araliphatic radical having at least 2 carbon atoms, and their pharmaceutically acceptable salts.

Aliphatic radicals R are, for example, lower alkyl having at least 2 carbon atoms, lower alkenyl, lower alkynyl, oxo-lower alkyl, hydroxy- or dihydroxy-lower alkyl, hydroxy-lower alkenyl, mono-, di- or poly-halo-lower alkyl, mono-, di- or poly-halo-lower alkenyl, mono-, di- or poly-halo(hydroxy)-lower alkyl, mono-, di- or poly-halo(hydroxy)-lower alkenyl, lower alkoxy-lower alkyl, di-lower alkoxy-lower alkyl, lower alkoxy(hydroxy)-lower alkyl, lower alkoxy(halo)-lower alkyl, lower alkylthio-lower alkyl and di-lower alkylthio-lower alkyl. Aliphatic radicals $R_1$, $R_2$ and $R_3$ are especially lower alkyl, including and especially methyl, lower alkenyl or lower alkynyl.

Cycloaliphatic radicals are, for example, cycloalkyl, and in the case of a cycloaliphatic radical R they are also hydroxycycloalkyl, oxa-, dioxa-, thia- and dithia-cycloalkyl.

Cycloaliphatic-aliphatic radicals are, for example, cycloalkyl-lower alkyl, cycloalkenyl-lower alkyl, mono-, di- or trihydroxycycloalkyl-lower alkyl, cycloalkyl(hydroxy)-lower alkyl and (lower alkylthio)cycloalkyl(hydroxy)-lower alkyl.

Araliphatic radicals are, for example, mono- or diphenyl-lower alkyl or naphthyl-lower alkyl each of which is unsubstituted or mono-, di- or tri-substituted by lower alkyl, lower alkoxy, hydroxy, halogen and/or by trifluoromethyl, preferably $\alpha$-phenyl-lower alkyl substituted as indicated or unsubstituted $\alpha,\alpha$-diphenyl- or $\alpha$-naphthyl-lower alkyl.

Heteroarylaliphatic radicals are, for example, thienyl-, furyl- or pyridyl-lower alkyl each of which is unsubstituted or substituted, especially mono- or di-substituted, by halogen, preferably unsubstituted $\alpha$-thienyl-, $\alpha$-furyl- or $\alpha$-pyridyl-lower alkyl.

Aromatic radicals are, for example, phenyl, which in the case of aromatic radicals $R_1$, $R_2$ and $R_3$ is preferably substituted, for example by halogen, lower alkyl, lower alkoxy and/or by trifluoromethyl, especially monosubstituted by halogen, and also naphthyl.

Hereinbefore and hereinafter, lower radicals and compounds are to be understood as being, for example, radicals and compounds having up to and including 7, preferably up to and including 4, carbon atoms (C atoms).

Lower alkyl R is, for example, $C_2$-$C_7$alkyl, preferably $C_3$-$C_5$alkyl, such as propyl, isopropyl, butyl, isobutyl, sec-butyl, tert-butyl or pentyl, but may also be a $C_6$-$C_7$alkyl group, such as a hexyl or heptyl group.

Lower alkyl $R_5$ is, for example, $C_1$-$C_7$alkyl, preferably $C_1$-$C_4$alkyl, such as methyl, ethyl, propyl, isopropyl or butyl, but may also be isobutyl, sec-butyl, tert-butyl or a $C_5$-$C_7$alkyl group, such as a pentyl, hexyl or heptyl group.

Lower alkenyl is, for example, $C_2$-$C_4$alkenyl, such as vinyl, allyl or but-2-enyl, but may also be a $C_5$-$C_7$alkenyl group, such as pentenyl, hexenyl or heptenyl.

Lower alkynyl is, for example, $C_2$-$C_7$alkynyl, preferably $C_3$-$C_5$alkynyl, that carries the double bond in a position higher than the $\alpha,\beta$-position, for example 2-propynyl (propargyl), but-3-yn-1-yl, but-2-yn-1-yl or pent-3-yn-1-yl.

Oxo-lower alkyl carries the oxo group preferably in a position higher than the $\alpha$-position and is, for example, oxo-$C_2$-$C_7$alkyl, especially oxo-$C_3$-$C_6$alkyl, such as 2-oxopropyl, 2- or 3-oxobutyl or 3-oxopentyl.

Hydroxy-lower alkyl carries the hydroxy groups preferably in the $\alpha$- or $\beta$-position and is, for example, corresponding hydroxy-$C_2$-$C_7$alkyl, such as 1-hydroxyethyl, 1- or 2-hydroxypropyl, 2-hydroxyprop-2-yl, 1- or 2-hydroxybutyl, 1-hydroxyisobutyl or 2-hydroxy-3-methylbutyl.

Dihydroxy-lower alkyl carries the hydroxy groups especially in the $\alpha,\beta$-position and is, for example, $\alpha,\beta$-dihydroxy-$C_3$-$C_7$alkyl, such as 1,2-dihydroxyprop-2-yl.

Hydroxy-lower alkenyl carries the hydroxy groups preferably in the $\alpha$-position and the double bond preferably in a position higher than the $\alpha,\beta$-position and is, for example, corresponding α-hydroxy-$C_3$–$C_5$alkenyl, for example 1-hydroxybut-2-enyl.

Mono-, di- or poly-halo-lower alkenyl is, for example, mono-, di- or tri-fluoro-$C_2$–$C_5$alkenyl, such as 1-fluorobut-2-enyl.

Mono-, di- or tri-halo(hydroxy)-lower alkyl carries the hydroxy group preferably in the α-position and the halogen atoms preferably in a position higher than the α-position and is, for example, corresponding mono-, di- or tri-fluoro-α-hydroxy-$C_2$–$C_7$alkyl, such as 4,4,4-tri-fluoro-1-hydroxybutyl.

Mono-, di- or poly-halo-lower alkyl is, for example, mono-, di- or tri-fluoro-$C_2$–$C_5$alkyl, such as 3,3,3-trifluoropropyl, 4,4,4-trifluorobutyl, 1- or 2-fluorobutyl or 1,1-difluorobutyl. Lower alkoxy is, for example, $C_1$–$C_7$alkoxy, preferably $C_1$–$C_4$alkoxy, such as methoxy, ethoxy, propoxy, isopropoxy or butoxy, but may also be isobutoxy, sec-butoxy, tert-butoxy or a $C_5$–$C_7$alkoxy group, such as a pentyloxy, hexyloxy or heptyloxy group.

Mono-, di- or tri-halo(hydroxy)-lower alkenyl carries the hydroxy group preferably in the α-position and the halogen atoms preferably in a position higher than the α-position and is, for example, corresponding mono-, di- or tri-fluoro-α-hydroxy-$C_2$–$C_5$alkenyl, such as 2-fluoro-1-hydroxybuten-2-yl.

Lower alkoxy-lower alkyl is, for example, $C_1$–$C_4$alkoxy-$C_1$–$C_4$alkyl, such as methoxy- or ethoxy-methyl, 2-methoxyethyl, 2-ethoxyethyl, 3-methoxy- or 3-ethoxy-propyl or 1- or 2-methoxybutyl.

Di-lower alkoxy-lower alkyl is, for example, di-$C_1$–$C_4$alkoxy-$C_1$–$C_4$alkyl, for example dimethoxymethyl, dipropoxymethyl, 1,1- or 2,2-diethoxyethyl, diisopropoxymethyl, dibutoxymethyl or 3,3-dimethoxypropyl.

Lower alkoxy(hydroxy)-lower alkyl is, for example, $C_1$–$C_4$alkoxy-$C_2$–$C_7$(hydroxy)alkyl, such as 2-hydroxy-3-methoxyprop-2-yl.

Lower alkoxy(halo)-lower alkyl is, for example, $C_1$–$C_4$alkoxy-$C_2$–$C_5$(halo)-lower alkyl, such as 2-fluoro-3-methoxybutyl.

Lower alkylthio-lower alkyl is, for example, $C_1$–$C_4$alkylthio-$C_1$–$C_4$alkyl, such as methylthio- or ethylthio-methyl, 2-methylthioethyl, 2-ethylthioethyl, 3-methylthio- or 3-ethylthio-propyl or 1- or 2-methylthiobutyl.

Di-lower alkylthio-lower alkyl is, for example, di-$C_1$–$C_4$alkylthio-$C_1$–$C_4$alkyl, for example dimethylthiomethyl, dipropylthiomethyl, 1,1- or 2,2-diethylthioethyl, diisopropylthiomethyl, dibutylthiomethyl or 3,3-dimethylthiopropyl.

Mono- or di-phenyl-lower alkyl is, for example, mono- or di-phenyl-$C_1$–$C_4$alkyl, such as benzyl, 1- or 2-phenylethyl or 2-phenylprop-2-yl, diphenylmethyl or, secondly, 2-phenylethyl, 2-phenylprop-1-yl or 3-phenylprop-1-yl.

Naphthyl-lower alkyl is, for example, naphthyl-$C_1$–$C_4$alkyl, such as 1- or 2-naphthylmethyl.

Thienyl-, furyl-or pyridyl-lower alkyl is, for example, thienyl-, furyl- or pyridyl-methyl, 1-thienyl-, 1-furyl- or 1-pyridyl-ethyl, 2-thienyl-, 2-furyl- or 2-pyridyl-prop-2-yl, or, secondly, 2-thienyl-, 2-furyl- or 2-pyridyl-ethyl, 2-thienyl-,2-furyl- or 2-pyridyl-prop-1-yl or 3-thienyl-, 3-furyl- or 3-pyridyl-prop-1-yl.

Halogen is, for example, halogen having an atomic number of up to and including 53, such as chlorine, iodine or fluorine, and also bromine.

Cycloalkyl is, for example, $C_3$–$C_8$cycloalkyl, especially $C_3$–$C_6$cycloalkyl, such as cyclopropyl, cyclobutyl, cyclopentyl or cyclohexyl.

Hydroxycycloalkyl is, for example, α-hydroxy-$C_3$–$C_6$-cycloalkyl, such as 1-hydroxycyclopropyl, 1-hydroxycyclobutyl or 1-hydroxycyclohexyl.

Oxa- or thia-cycloalkyl is, for example, oxa- or thia-$C_3$–$C_8$cycloalkyl, especially oxa- or thia-$C_3$–$C_6$cycloalkyl, such as 2-oxacyclopropyl (oxiranyl), 2- or 3-oxacyclobutyl (oxetanyl), 2- or 3-thiacyclobutyl (thietanyl), 2- or 3-oxacyclopentyl (tetrahydrofuranyl), 2- or 3-thiacyclopentyl (thiolanyl) or 2-oxacyclohexyl (tetrahydropyranyl).

Dioxacycloalkyl is, for example, 1,3-dioxa-$C_3$–$C_8$cycloalkyl, such as 1,3-dioxolan-2-yl or 1,3-dioxan-2-yl.

Dithiacycloalkyl is, for example, 1,3-dithia-$C_3$–$C_8$cycloalkyl, such as 1,3-dithiolan-2-yl or 1,3-dithian-2-yl.

Cycloalkyl-lower alkyl is, for example, $C_3$–$C_8$cycloalkyl-$C_1$–$C_4$alkyl, especially $C_3$–$C_6$cycloalkyl-$C_1$–$C_4$alkyl, such as α-($C_3$–$C_6$cycloalkyl)-$C_1$–$C_4$alkyl, for example cyclopropylmethyl, cyclobutylmethyl, cyclopentylmethyl or cyclohexylmethyl.

Cycloalkenyl-lower alkyl is, for example, $C_3$–$C_8$-, especially $C_3$–$C_6$cycloalkenyl-$C_1$–$C_4$alkyl, such as α-($C_3$–$C_6$cycloalkenyl)-$C_1$–$C_4$alkyl, for example cyclohex-3-enyl.

Mono-, di- or trihydroxycycloalkyl-lower alkyl is, for example, mono-, di- or trihydroxy-$C_3$–$C_8$, especially mono-, di- or trihydroxy-$C_3$–$C_6$cycloalkyl-$C_1$–$C_4$alkyl, such as α-(mono-, di- or trihydroxy-$C_3$–$C_6$cycloalkyl)-$C_1$–$C_4$alkyl, for example 3,4-dihydroxycyclohexylmethyl or 3,4,5-trihydroxycyclohexylmethyl.

Cycloalkyl(hydroxy)-lower alkyl is, for example, $C_3$–$C_6$cycloalkyl-$C_1$–$C_4$(hydroxy)alkyl, such as α-($C_3$–$C_6$cycloalkyl)-α-hydroxy-$C_1$–$C_4$alkyl, for example cyclopropyl(hydroxy)methyl, cyclobutyl(hydroxy)methyl or cyclohexyl(hydroxy)methyl.

(Lower alkylthiocycloalkyl)(hydroxy)-lower alkyl is, for example, 1-($C_1$–$C_4$alkylthio-$C_3$–$C_6$cycloalkyl)-1-hydroxy-$C_1$–$C_4$alkyl, such as (2-methylthiocycloprop-1-yl)hydroxymethyl.

On account of their amphoteric nature, the compounds of formula I are in the form of internal salts and can form both acid addition salts and salts with bases.

Acid addition salts of compounds of formula I are, for example, pharmaceutically acceptable salts thereof with suitable mineral acids, such as hydrohalic acids, sulfuric acid or phosphoric acid, for example hydrochlorides, hydrobromides, sulfates, hydrogen sulfates or phosphates, or salts with suitable aliphatic or aromatic sulfonic acids or N-substituted sulfamic acids, for example methanesulfonates, benzenesulfonates, p-toluenesulfonates or N-cyclohexylsulfaminates (cyclamates).

Salts of compounds of formula I with bases are, for example, salts thereof with pharmaceutically acceptable bases, such as non-toxic metal salts derived from metals of groups Ia, Ib, IIa and IIb, for example alkali metal salts, especially sodium or potassium salts, alkaline earth metal salts, especially calcium or magnesium salts, and also ammonium salts with ammonia or organic amines or quaternary ammonium bases, such as unsubstituted or C-hydroxylated aliphatic amines, especially mono-, di- or tri-lower alkylamines, for example methyl-, ethyl- or diethyl-amine, mono-, di- or tri-(hydroxy-lower alkyl)amines, such as ethanol-, diethanol- or triethanol-amine, tris(hydroxymethyl)methylamine or 2-hydroxy-tert-butylamine, or N-(hydroxy-lower alkyl)-N,N-di-lower alkylamines or N-(polyhydroxy-lower alkyl)- lower alkylamines, such as 2-(dimethylamino)ethanol or D-glucamine, or quaternary aliphatic ammonium hydroxides, for example tetrabutylammonium hydroxide.

Depending upon the presence of asymmetric carbon atoms, the compounds according to the invention may be in the form of isomeric mixtures, especially of racemates, or in the form of pure isomers, especially of optical antipodes.

Compounds of formula I wherein one of the radicals $R_1$, $R_2$ and $R_3$ is hydrogen or an aliphatic, cycloaliphatic, araliphatic or aromatic radical, another is hydrogen or, in the case of $R_1$ or $R_2$, hydroxy, and the remaining radical is hydrogen, and wherein $R_1'$, $R_2'$, $R_4$ and $R_5$ are hydrogen, and their pharmaceutically acceptable salts and their $GABA_B$-antagonistic properties, are known and have already been proposed as nootropic, anxiolytic and anti-depressive active ingredients in medicaments.

The novel compounds of formula I and their pharmaceutically acceptable salts also have valuable $GABA_B$-antagonistic properties. In particular, they exhibit effective binding to the $GABA_B$-receptor and prove to be antagonists of GABA ($\gamma$-aminobutyric acid) at that receptor. From the point of view of mechanism, antagonism to $GABA_B$-receptors can increase the release of rapid stimulus amino acid transmitters, that is to say glutamate and aspartate, and thus improve the processing of information in the brain. In line with this is the discovery that the late postsynaptic inhibition potential in the hippocampus, which is attributed to a $GABA_B$-mechanism, is broken down by the antagonists and thus allows a more rapid nerve impulse transmission sequence.

On the other hand, it has been found that chronic treatment with anti-depressants and repeated electric shocks increases the number of $GABA_B$-receptors in the cerebral cortex of rats. In accordance with receptor theories, chronic treatment with $GABA_B$-antagonists should produce the same effect. For this and other reasons, therefore, $GABA_B$-antagonists can act as anti-depressants.

The novel $GABA_B$-antagonists according to the invention interact at the $GABA_B$-receptor with $IC_{50}$ values of approximately $10^{-8}M$ (moles/l) and above in cerebral cortex membranes of rats. In contrast to $GABA_B$-agonists such as baclofen, they do not potentiate the stimulation of adenylate cyclase by noradrenalin in sections of rat cerebral cortex, but act as an antagonist to the action of baclofen. The antagonism to baclofen can also be demonstrated in vitro in electrophysiological models, for example the penecillin-induced "epileptic" hippocampus section preparation, where baclofen in a concentration of 6 $\mu$M (micromoles/liter) inhibits "epilepsy-like" discharges of pyramidal cells. The compounds according to the invention act as an antagonist to baclofen action at concentrations of from approximately 10 to approximately 100 $\mu$M (micromoles/liter). In vivo, the antagonism can be demonstrated by iontophoresis of baclofen in the cerebral cortex of rats and by systemic administration of antagonists in doses of from 10 to 100 mg/kg. At doses of approximately 30 mg/kg, antagonism to the muscle-relaxing action of baclofen occurs, which is measured in the Rotarod model.

The novel $GABA_B$-antagonists not only exhibit antagonism to baclofen, but also exhibit an independent action as antagonists to endogenous GABA. Accordingly, the antagonists are active in conventional behavioural models which are characteristic of anti-depressive, anxiolytic and/or nootropic properties. It has been found that compounds of formula I are active on oral administration in the floating test according to Porsolt, in the Geller test, the delayed passive avoidance test (single-attempt modification) in pre-test and post-test situations, in the two-chamber test and in the complex labyrinth. Moreover, in studies on Rhesus monkeys an increased play instinct, curiosity, social grooming behaviour and a reduction in anxiety symptoms were observed.

The novel compounds of formula I and their pharmaceutically acceptable salts are therefore excellently suitable as nootropics, anti-depressants and anxiolytics, for example for the treatment of symptoms of cerebral insufficiency, emotional depression and anxiety conditions.

On account of the antagonism of the known $GABA_B$-antagonists to baclofen, it has hitherto been assumed that $GABA_B$-antagonists, such as compounds of formula I, do not have an anti-epileptic activity component.

Surprisingly, it has now been found that $GABA_B$-antagonists, especially compounds of formula I, have pronounced anti-absence properties in vivo.

These properties can be demonstrated in a particular strain of rats on the basis of their pronounced inhibitory action on spontaneous "spike and wave" discharges in the following animal model for absence epilepsy.

Approximately 30% of the Wistar rats reared at the Centre de Neurochimie in Strasbourg exhibit spontaneous changes in behaviour, of which electroencephalograms (EEG) and symptoms are comparable to those of human absences (petit mal). Synchronous "spike and wave" discharges (SWD; frontopariental cortex; 7-8 Hz; 300-1000 $\mu$V, duration 0.5 to 40 s, mean value=6.0±3.4 s) and frequently myoclonia facialis accompany a cessation of behaviour. These absence-like conditions occur spontaneously and repeatedly. By selective rearing of these rats it was possible to obtain a strain in which 100% of the rats exhibit these SWD (epileptic rats). In contrast, a strain could be reared in which 100% of the rats are SWD-free (control rats). This pharmacological model is described in Vergnes M., Marescaux C., Micheletti G., Reis J., Depaulis A., Rumbach L. and Warter J. M., Neurosci. Lett. 33. 97–101 (1982).

In this model, for example, the clinically used anti-epileptics ethosuximide, diazepam, trimethadione and sodium valproate in doses $\geq$25 mg/kg (ethosuximide), $\geq$0.5 mg/kg (diazepam) and $\geq$50 mg/kg (trimethadione and sodium valproate) reduce the spike and wave discharges in dose-dependent manner. Carbamazepine and phenytoin are ineffective or make the attacks worse at high doses. Phenobarbital is effective at from 2.5 to 10 mg/kg and is ineffective at 20 mg/kg. The action of these anti-epileptics on the crises in rats and absences in humans supports the hypothesis that this animal model represents a pharmacological model for absence epilepsy. Its predictive value appears to be at least as good as that of other customary animal models.

The compounds of formula I and their pharmaceutically acceptable salts, as well as being suitable as nootropics, anti-depressants and anxiolytics, are therefore excellently suitable as active ingredients in anti-epileptic medicaments for the treatment of epilepsies of the "petit mal" type, both of spontaneous absence epilepsies, such as spontaneous absence epilepsies in childen and young people, and atypical absences, such as absences of the Lennox-Gastaut syndrome, and also of absences that occur as undesired side effects in the case of treatment with conventional "grand mal" anti-epileptics, such as phenytoin, carbamazepine or Vigabatrin ® and anti-epileptics having the same or a similar activity profile.

The invention relates, for example, to the use of compounds of formula I wherein
a) $R_1$ and $R_1'$ are hydrogen, $R_2$ is an aliphatic, cycloaliphatic, araliphatic or aromatic radical and $R_2'$ is hydrogen or hydroxy, or $R_2$ is hydroxy and $R_2'$ is hydrogen, or $R_2$ and $R_2'$ together form an oxo group, and $R_3$, $R_4$ and $R_5$ are hydrogen, or
b) $R_1$ is hydroxy or an aliphatic, cycloaliphatic, araliphatic or aromatic radical and $R_1'$, $R_2$, $R_2'$, $R_3$, $R_4$ and $R_5$ are hydrogen, or
c) $R_1$ is halogen, $R_1'$ is hydrogen or halogen and $R_2$, $R_2'$, $R_3$, $R_4$ and $R_5$ are hydrogen,
wherein R is an aliphatic, cycloaliphatic, cycloaliphatic-aliphatic, araliphatic or aromatic radical having at least 2 carbon atoms or, when $R_1$ is hydrogen or hydroxy, $R_2$ is an aromatic radical and $R_1'$, $R_2'$ and $R_3$ are hydrogen, R is methyl, and their pharmaceutically acceptable salts as anti-epileptics and for the preparation of an anti-epileptic for the treatment of epilepsies of the "petit mal" type, to anti-epileptic medicaments comprising those compounds and a process for the preparation of such medicaments, and to a method, characterised by the administration of such a medicament, of treating epileptic disorders of the "petit mal" type.

The invention relates especially to the use of compounds of formula I wherein one of the radicals $R_1$, $R_2$ and $R_3$ is hydrogen, lower alkyl, lower alkenyl, lower alkynyl, cycloalkyl, or phenyl-lower alkyl, diphenyl-lower alkyl or naphthyl-lower alkyl each of which is unsubstituted or mono- or poly-substituted in the phenyl or naphthyl moiety by lower alkyl, lower alkoxy, halogen and/or by trifluoromethyl, or phenyl or naphthyl each of which is unsubstituted or substituted by halogen, lower alkyl, lower alkoxy and/or by trifluoromethyl, another radical is hydrogen or, in the case of $R_1$ or $R_2$, hydroxy or, in the case of $R_1$, halogen or, in the case of $R_2$ together with $R_2'$, oxo, and the remaining radical is hydrogen, $R_1'$ is hydrogen or halogen, $R_2'$ is hydrogen, hydroxy or, together with $R_2$, is oxo, $R_4$ and $R_5$ are hydrogen, or $R_4$ is phenyl-lower alkyl, diphenyl-lower alkyl, naphthyl-lower alkyl, thienyl-lower alkyl, furyl-lower alkyl or pyridyl-lower alkyl each of which is unsubstituted or mono- or poly-substituted in the phenyl, naphthyl, thienyl, furyl or pyridyl moiety by lower alkyl, lower alkoxy, halogen and/or by trifluoromethyl, and $R_5$ is hydrogen, lower alkyl, lower alkenyl, lower alkynyl or a group $R_4$, and R is lower alkyl having at least 2 carbon atoms, lower alkenyl, lower alkynyl, cycloalkyl, cycloalkyl-lower alkyl, cycloalkenyl-lower alkyl, mono-, di- or trihydroxycycloalkyl-lower alkyl, cycloalkyl(hydroxy)-lower alkyl, (lower alkylthio)cycloalkyl(hydroxy)-lower alkyl, or phenyl- or naphthyl-lower alkyl each of which is unsubstituted or mono- or poly-substituted in the phenyl or naphthyl moiety by lower alkyl, lower alkoxy, halogen and/or by trifluoromethyl, or phenyl or naphthyl each of which is unsubstituted or substituted by halogen, lower alkyl, lower alkoxy and/or by trifluoromethyl, or, when $R_1$ is hydrogen or hydroxy, $R_2$ is an aromatic radical and $R_1'$, $R_2'$ and $R_3$ are hydrogen, R is methyl, and their pharmaceutically acceptable salts as anti-epileptics for the treatment of epilepsies of the "petit mal" type and for suppressing "petit mal"-type conditions arising from known anti-epileptics, and for the preparation of an anti-epileptic for the treatment of epilepsies of the "petit mal" type, to anti-epileptic medicaments comprising those compounds and a process for the preparation of such medicaments, and to a method, characterised by the administration of such a medicament, of treating epileptic disorders of the "petit mal" type and of suppressing the mentioned "petit mal"-type conditions arising from known anti-epileptics, and also to compounds of formula I wherein $R_1$, $R_1'$, $R_2'$ and $R_3$ are hydrogen, $R_2$ is hydrogen or hydroxy, $R_4$ is a phenyl-, diphenyl- or naphthyl-lower alkyl radical each of which is unsubstituted or mono-, di- or tri-substituted in the phenyl or naphthyl moiety by lower alkyl, lower alkoxy, hydroxy and/or by halogen, or is a thienyl-, furyl- or pyridyl-lower alkyl radical each of which is unsubstituted or halo-substituted in the thienyl, furyl or pyridyl moiety, $R_5$ is hydrogen, lower alkyl or a group $R_4$, and R is lower alkyl having at least 2 carbon atoms, lower alkenyl, lower alkynyl, oxo-lower alkyl, hydroxy- or dihydroxy-lower alkyl, hydroxy-lower alkenyl, mono-, di- or poly-halo-lower alkyl, mono-, di- or poly-halo-lower alkenyl, mono-, di- or poly-halo(hydroxy)-lower alkyl, mono-, di- or poly-halo(hydroxy)-lower alkenyl, lower alkoxy-lower alkyl, di-lower alkoxy-lower alkyl, lower alkoxy(hydroxy)-lower alkyl, lower alkoxy(halo)-lower alkyl, lower alkylthio-lower alkyl, di-lower alkylthio-lower alkyl, cycloalkyl, hydroxycycloalkyl, oxa-, dioxa-, thia- and dithia-cycloalkyl, cycloalkyl-lower alkyl, cycloalkenyl-lower alkyl, mono-, di- or trihydroxycycloalkyl-lower alkyl, cycloalkyl(hydroxy)-lower alkyl and (lower alkylthio)cycloalkyl(hydroxy)-lower alkyl, or mono- or di-phenyl-lower alkyl or naphthyl-lower alkyl each of which is unsubstituted or mono-, di-or tri-substituted by lower alkyl, lower alkoxy, halogen, hydroxy and/or by trifluoromethyl, or unsubstituted or halo-substituted thienyl-, furyl- or pyridyl-lower alkyl, and their salts, especially their pharmaceutically acceptable salts, as such.

The invention relates especially, for example, to the use of compounds of formula I wherein
a) $R_1$ and $R_1'$ are hydrogen, $R_2$ is an aliphatic, cycloaliphatic, araliphatic or aromatic radical and $R_2'$ is hydrogen or hydroxy, or $R_2$ is hydroxy and $R_2'$ is hydrogen, or $R_2$ and $R_2'$ together form an oxo group, and $R_3$, $R_4$ and $R_5$ are hydrogen, or
b) $R_1$ is hydroxy or an aliphatic, cycloaliphatic, araliphatic or aromatic radical and $R_1'$, $R_2$, $R_2'$, $R_3$, $R_4$ and $R_5$ are hydrogen, or
c) $R_1$ is halogen, $R_1'$ is hydrogen or halogen and $R_2$, $R_2'$, $R_3$, $R_4$ and $R_5$ are hydrogen,
wherein R is an aliphatic, cycloaliphatic, cycloaliphatic-aliphatic, araliphatic or aromatic radical having at least 2 carbon atoms or, when $R_1$ is hydrogen or hydroxy, $R_2$ is an aromatic radical and $R_1'$, $R_2'$ and $R_3$ are hydrogen, R is methyl, and their pharmaceutically acceptable salts as anti-epileptics and for the preparation of an anti-epileptic for the treatment of epilepsies of the "petit mal" type, to anti-epileptic medicaments comprising those compounds and a process for the preparation of such medicaments, and to a method, characterised by the administration of such a medicament, of treating epileptic disorders of the "petit mal" type, and also to compounds of formula I wherein $R_1$, $R_1'$, $R_2'$ and $R_3$ are hydrogen, $R_2$ is hydrogen or hydroxy, $R_4$ is a phenyl- or naphthyl-lower alkyl radical each of which is unsubstituted or substituted by lower alkyl, lower alkoxy and- /or by halogen, or an unsubstituted or halo-substituted thienyl-, furyl- or pyridyl-lower alkyl radical, $R_5$ is hydrogen, lower alkyl or a group $R_4$, and R is lower alkyl having at least 2 carbon atoms, lower alkenyl, lower alkynyl, oxo-lower alkyl, hydroxy- or dihydroxy-lower alkyl, hydroxy-lower alkenyl, mono-, di- or polyhalo-lower alkyl, mono-, di- or poly-halo-lower alkenyl, mono-, di- or poly-halo(hydroxy)-lower alkyl, mono-, di- or poly-halo(hydroxy)-lower alkenyl, lower alkoxy-lower alkyl, di-lower alkoxy-lower alkyl, lower alkoxy(hydroxy)-lower alkyl, lower alkoxy(halo)-lower alkyl, lower alkylthio-lower alkyl, di-lower alkylthio-lower alkyl, cycloalkyl, hydroxycycloalkyl, oxa-, dioxa-, thia- and dithia-cycloalkyl, cycloalkyl(hydroxy)-lower alkyl and (lower alkylthio)cycloalkyl(hydroxy)-lower alkyl, or phenyl-lower alkyl or naphthyl-lower alkyl each of which is unsubstituted or mono- or di-substituted by lower alkyl, lower alkoxy, halogen and/or by trifluoromethyl, and their salts, especially their pharmaceutically acceptable salts.

The invention relates more especially to the use of compounds of formula I wherein one of the radicals $R_1$, $R_2$ and $R_3$ is hydrogen, $C_1$–$C_4$alkyl, $C_3$–$C_6$cycloalkyl, phenyl- or naphthyl$C_1$–$C_4$alkyl that is unsubstituted or mono- or poly-substituted in the phenyl or naphthyl moiety by $C_1$–$C_4$alkyl, $C_1$–$C_4$alkoxy, halogen and/or by trifluoromethyl, or is phenyl or naphthyl either of which is unsubstituted or mono- or poly-substituted in the phenyl or naphthyl moiety by $C_1$–$C_4$alkyl, $C_1$–$C_4$alkoxy, halogen and/or by trifluoromethyl, another radical is hydrogen or, in the case of $R_1$ or $R_2$, hydroxy, and the remaining radical is hydrogen, $R_1'$ is hydrogen, $R_2'$ is hydrogen, hydroxy or, together with $R_2$, is oxo, $R_4$ and $R_5$ are hydrogen, or $R_4$ is a phenyl-$C_1$–$C_4$alkyl radical that is unsubstituted or mono- or poly-substituted in the phenyl moiety by $C_1$–$C_4$alkyl, $C_1$–$C_4$alkoxy, halogen and/or by trifluoromethyl, and $R_5$ is hydrogen, $C_1$–$C_4$alkyl or a group $R_4$, and R is $C_2$–$C_7$alkyl, $\alpha,\alpha$-di-$C_1$–$C_4$alkoxy-$C_2$–$C_7$alkyl, $\alpha,\alpha$-dihalo-$C_2$–$C_7$alkyl, $C_3$–$C_6$cycloalkyl, $C_3$–$C_6$cycloalkyl-$C_1$–$C_4$alkyl, $C_3$–$C_6$cycloalkenyl-$C_1$–$C_4$alkyl, such as $\alpha$-($C_3$–$C_6$cycloalkenyl)-$C_1$–$C_4$alkyl, for example, cyclohex-3-enyl, mono-, di- or trihydroxy-$C_3$–$C_6$cycloalkyl-$C_1$–$C_4$alkyl, such as $\alpha$-(mono-, di- or trihydroxy-$C_3$–$C_6$-cycloalkyl)-$C_1$–$C_4$alkyl, for example, 3,4-dihydroxycyclohexylmethyl or 3,4,5-trihydroxycyclohexylmethyl, benzyl or, when $R_2$ is halophenyl and $R_1$, $R_1'$, $R_2'$ and $R_3$ are hydrogen, R is methyl, and their pharmaceutically acceptable salts as anti-epileptics for the treatment of epilepsies of the "petit mal" type and for suppressing "petit mal"-type conditions arising from known anti-epileptics, and for the preparation of an anti-epileptic for the treatment of epilepsies of the "petit mal" type, to anti-epileptic medicaments comprising those compounds and a process for the preparation of such medicaments, and to a method, characterised by the administration of such a medicament, of treating epileptic disorders of the "petit mal" type and of suppressing the mentioned "petit mal"-type conditions arising from known anti-epileptics, and also to compounds of formula I wherein R is $C_3$–$C_7$alkyl, such as propyl, isopropyl, butyl, isobutyl or pentyl, $\alpha,\alpha$-di-$C_1$–$C_4$-alkoxy-$C_1$–$C_4$alkyl, especially $\alpha,\alpha$-di-$C_1$–$C_4$alkoxymethyl, such as dimethoxy- or diethoxy-methyl, $C_3$–$C_6$cycloalkyl-$C_1$–$C_4$alkyl, such as cyclopropyl- or cyclohexyl-methyl, $C_3$–$C_6$cycloalkenyl-$C_1$–$C_4$alkyl, such as $\alpha$-($C_3$–$C_6$cycloalkenyl)-$C_1$–$C_4$alkyl, for example, cyclohex-3-enyl, mono-, di- or trihydroxy-$C_3$–$C_6$cycloalkyl-$C_1$–$C_4$alkyl, such as $\alpha$-(mono-, di- or trihydroxy-$C_3$–$C_6$cycloalkyl)-$C_1$–$C_4$alkyl, for example, 3,4-dihydroxycyclohexylmethyl or 3,4,5-trihydroxycyclohexylmethyl, or benzyl that is unsubstituted or mono-, di- or tri-substituted by $C_1$–$C_4$alkyl, such as methyl, $C_1$–$C_4$alkoxy, such as methoxy, hydroxy and/or by halogen, such as fluorine, chlorine or iodine, $R_1$ is hydrogen or hydroxy, $R_2$ is phenyl- or diphenyl-$C_1$–$C_4$alkyl, such as benzyl, 1-phenylethyl or 2-phenylprop-2-yl, each of which is unsubstituted or mono-, di- or tri-substituted by $C_1$–$C_4$alkyl, such as methyl, $C_1$–$C_4$alkoxy, such as methoxy, and/or by halogen, such as fluorine, chlorine or iodine, or is naphthyl-$C_1$–$C_4$alkyl, such as 1- or 2-naphthylmethyl, thienyl-$C_1$–$C_4$alkyl, such as thienylmethyl, furyl-$C_1$–$C_4$alkyl, such as furylmethyl, or pyridyl-$C_1$–$C_4$alkyl, such as pyridylmethyl, each of which is unsubstituted or monosubstituted by halogen having an atomic number of up to and including 35, such as chlorine, and $R_3$ is hydrogen, $C_1$–$C_4$alkyl, such as methyl, or a group $R_2$, and their salts, especially their pharmaceutically acceptable salts, as such.

The invention relates more especially to the use, for example, of compounds of formula I wherein a) $R_1$, $R_1'$, $R_2'$, $R_3$, $R_4$ and $R_5$ are hydrogen, $R_2$ is $C_1$–$C_4$alkyl, $C_3$–$C_6$cycloalkyl, benzyl, phenyl, halophenyl or naphthyl and $R_2'$ is hydrogen or hydroxy, or $R_2$ is hydroxy and $R_2'$ is hydrogen, or $R_2$ and $R_2'$ together form an oxo group, or b) $R_1$ is hydroxy, $C_1$–$C_4$alkyl, $C_3$–$C_6$cycloalkyl, benzyl, phenyl, halophenyl or naphthyl, and $R_1'$, $R_2$, $R_3$, $R_4$ and $R_5$ are hydrogen, or c) $R_1$ is halogen, $R_1'$ is hydrogen or halogen and $R_2$, $R_2'$, $R_3$, $R_4$ and $R_5$ are hydrogen, and R is $C_2$–$C_7$alkyl, $\alpha,\alpha$-di-$C_1$–$C_4$alkoxy-$C_2$–$C_7$alkyl, $\alpha,\alpha$-dihalo-$C_2$–$C_7$alkyl, $C_3$–$C_6$cycloalkyl, $C_3$–$C_6$cycloalkyl-$C_1$–$C_4$alkyl, benzyl or, when $R_2$ is halophenyl or naphthyl and $R_1$, $R_1$, $R_2'$ and $R_3$ are hydrogen, R is methyl, and their pharmaceutically acceptable salts as anti-epileptics and for the preparation of an anti-epileptic for the treatment of epilepsies of the "petit mal" type, to anti-epileptic medicaments comprising those compounds and a process for the preparation of such medicaments, and to a method, characterised by the administration of such a medicament, of treating epileptic disorders of the "petit mal" type, and also to compounds of formula I wherein $R_1$, $R_1'$, $R_2'$ and $R_3$ are hydrogen, $R_2$ is hydrogen or hydroxy, $R_4$ is phenyl-$C_1$–$C_4$alkyl, such as benzyl, 1-phenylethyl or 2-phenylprop-2-yl, that is unsubstituted or monosubstituted by $C_1$–$C_4$alkyl, such as methyl, or $C_1$–$C_4$alkoxy, such as methoxy, or mono- or di-substituted by halogen having an atomic number of up to and including 35, such as chlorine, or is naphthyl-, thienyl-, furyl- or pyridyl-$C_1$–$C_4$alkyl, such as 1- or 2-naphthyl-, thienyl-, furyl- or pyridyl-methyl, each of which is unsubstituted or monosubstituted by halogen having an atomic number of up to and including 35, such as chlorine, $R_5$ is hydrogen, $C_1$–$C_4$alkyl, such as methyl, or a group $R_4$, and R is $C_3$–$C_7$alkyl, such as propyl, isopropyl, butyl, isobutyl or pentyl, $\alpha,\alpha$-di-$C_1$–$C_4$alkoxy-$C_1$–$C_4$alkyl, especially $\alpha,\alpha$-di-$C_1$–$C_4$alkoxymethyl, such as dimethoxy- or diethoxy-methyl, $C_3$–$C_6$cycloalkyl-$C_1$–$C_4$alkyl, such as cyclopropyl- or cyclohexyl-methyl, or benzyl that is unsubstituted or substituted by $C_1$–$C_4$alkyl, such as methyl, $C_1$–$C_4$alkoxy, such as methoxy, or by halogen having an atomic number of up to and including 35, such as chlorine, and their salts, especially their pharmaceutically acceptable salts, as such.

The invention relates very especially to the use of compounds of formula I wherein $R_1$, $R_1'$, $R_2'$ and $R_3$ are hydrogen, $R_2$ is hydrogen or hydroxy, $R_4$ and $R_5$ are hydrogen, or $R_4$ is a phenyl-$C_1$-$C_4$alkyl radical, such as a benzyl radical, that it unsubstituted or mono- or poly-substituted in the phenyl moiety by $C_1$-$C_4$alkyl, such as methyl, $C_1$-$C_4$alkoxy, such as methoxy, halogen, such as chlorine, and/or by trifluoromethyl, and $R_5$ is hydrogen or $C_1$-$C_4$alkyl, such as methyl or ethyl, and R is $C_2$-$C_7$alkyl, such as butyl, $\alpha,\alpha$-di-$C_1$-$C_4$-alokoxy-$C_1$-$C_4$alkyl, such as diethoxymethyl, $\alpha,\alpha$-dihalo-$C_2$-$C_7$alkyl, such as 1,1-difluorobutyl, $C_3$-$C_6$cycloalkyl, such as cyclohexyl, $C_3$-$C_6$cycloalkyl-$C_1$-$C_4$alkyl, such as cyclohexylmethyl, or is a phenyl-$C_1$-$C_4$alkyl radical, such as a benzyl or 1-phenylethyl radical, that is unsubstituted or mono- or poly-substituted in the phenyl moiety by $C_1$-$C_4$alkyl, such as methyl, $C_1$-$C_4$alkoxy, such as methoxy, halogen, such as chlorine, and/or by trifluoromethyl, and their pharmaceutically acceptable salts as anti-epileptics for the treatment of epilepsies of the "petit mal" type and for suppressing "petit mal"-type conditions arising from known anti-epileptics, and for the preparation of an anti-epileptic for the treatment of epilepsies of the "petit mal" type, to anti-epileptic medicaments comprising those compounds and a process for the preparation of such medicaments, and to a method, characterised by the administration of such a medicament, of treating epileptic disorders of the "petit mal" type and of suppressing the mentioned "petit mal"-type conditions arising from known anti-epileptics, and also to compounds of formula I wherein $R_1$, $R_1'$, $R_2'$ and $R_3$ are hydrogen, $R_2$ is hydrogen or hydroxy, $R_4$ is $\alpha$-phenyl-$C_1$-$C_4$alkyl, such as benzyl, 1-phenylethyl or 2-phenylprop-2-yl, that is unsubstituted or mono- or di-substituted by halogen having an atomic number of up to and including 35, such as chlorine, or is unsubstituted $\alpha$-naphthyl-$C_1$-$C_4$alkyl, such as 1- or 2-naphthylmethyl, $\alpha$-thienyl-$C_1$-$C_4$alkyl, such as thienylmethyl, $\alpha$-furyl-$C_1$-$C_4$alkyl, such as furylmethyl, or $\alpha$-pyridyl-$C_1$-$C_4$alkyl, such as pyridylmethyl, $R_5$ is hydrogen, $C_1$-$C_4$alkyl, such as methyl, or a group $R_4$, and R is $C_3$-$C_5$alkyl, such as butyl, $\alpha,\alpha$-di-$C_1$-$C_4$alkoxymethyl, such as diethoxymethyl, $C_3$-$C_6$cycloalkyl-$C_1$-$C_4$alkyl, such as cyclopropyl- or cyclohexyl-methyl, $C_3$-$C_6$cycloalkenyl-$C_1$-$C_4$alkyl, such as $\alpha$-($C_3$-$C_6$cycloalkenyl)-$C_1$-$C_4$alkyl, for example, cyclohex-3-enyl, mono-, di- or trihydroxy-$C_3$-$C_6$cycloalkyl-$C_1$-$C_4$alkyl, such as $\alpha$-(mono-, di- or trihydroxy-$C_3$-$C_6$cycloalkyl)-$C_1$-$C_4$alkyl, for example, 3,4-dihydroxycyclohexylmethyl or 3,4,5-trihydroxycyclohexylmethyl, or benzyl, and their salts, especially their pharmaceutically acceptable salts, as such.

The invention relates very especially, for example, to the use of compounds of formula I wherein $R_1$, $R_1'$, $R_2'$, $R_3$, $R_4$ and $R_5$ are hydrogen, $R_2$ is hydrogen or hydroxy and R is $C_2$-$C_7$alkyl, $\alpha,\alpha$-di-$C_1$-$C_4$alkoxy-$C_1$-$C_4$alkyl, such as diethoxymethyl, $\alpha,\alpha$-dihalo-$C_2$-$C_7$alkyl, such as 1,1-difluorobutyl, $C_3$-$C_6$cycloalkyl, such as cyclohexyl, $C_3$-$C_6$cycloalkyl-$C_1$-$C_4$alkyl, such as cyclohexylmethyl, or benzyl, and their pharmaceutically acceptable salts as anti-epileptics and for the preparation of an anti-epileptic for the treatment of epilepsies of the "petit mal" type, to anti-epileptic medicaments comprising those compounds and a process for the preparation of such medicaments, and to a method, characterised by the administration of such a medicament, of treating epileptic disorders of the "petit mal" type, and also to compounds of formula I wherein $R_1$, $R_1'$, $R_2'$ and $R_3$ are hydrogen, $R_2$ is hydrogen or hydroxy, $R_4$ is phenyl-$C_1$-$C_4$alkyl, such as benzyl, 1-phenylethyl or 2-phenyl-prop-2-yl, that is unsubstituted or mono- or di-substituted by halogen having an atomic number of up to and including 35, such as chlorine, or is unsubstituted naphthyl-, thienyl-, furyl- or pyridyl-$C_1$-$C_4$alkyl, such as 1- or 2-naphthyl-, thienyl-, furyl- or pyridyl-methyl, $R_5$ is hydrogen, $C_1$-$C_4$alkyl, such as methyl, or a group $R_4$, and R is $C_3$-$C_5$alkyl, such as butyl, $\alpha,\alpha$-di-$C_1$-$C_4$alkoxymethyl, such as diethoxymethyl, $C_3$-$C_6$cycloalkyl-$C_1$-$C_4$alkyl, such as cyclopropyl- or cyclohexylmethyl, or benzyl, and their salts, especially their pharmaceutically acceptable salts, as such.

The invention relates specifically to the use of the known compounds listed below:

3-aminopropyl(cyclohexylmethyl)phosphinic acid,
3-aminopropyl(n-butyl)phosphinic acid,
3-aminopropyl(diethoxymethyl)phosphinic acid,
3-aminopropyl(benzyl)phosphinic acid,
3-aminopropyl(1,1-difluorobutyl)phosphinic acid,
3-amino-2-(p-chlorophenyl)propyl(methyl)phosphinic acid,
3-amino-2-hydroxypropyl(cyclohexylmethyl)phosphinic acid,
3-amino-2(S)-hydroxypropyl(cyclohexylmethyl)phosphinic acid,
3-amino-2(R)-hydroxy-propyl(cyclohexylmethyl)phosphinic acid and
3-amino-2(S)-hydroxypropyl(benzyl)phosphinic acid
and their pharmaceutically acceptable salts as anti-epileptics and for the preparation of an anti-epileptic for the treatment of epilepsies of the "petit mal" type, to anti-epileptic medicaments comprising those compounds and a process for the preparation of such medicaments, and to a method, characterised by the administration of such a medicament, of treating epileptic disorders of the "petit mal" type, and also to the compounds mentioned in the Preparation Examples, specifically 3-(p-chlorobenzylamino)propyl(diethoxymethyl)phosphinic acid,
3-(p-chlorobenzylamino)-2(S)-hydroxypropyl(benzyl)-phosphinic acid,
3-(p-chlorobenzylamino)-2-hydroxypropyl(n-butyl)-phosphinic acid,
3-(3,4-dichlorobenzylamino)-2(S)-hydroxypropyl(benzyl)phosphinic acid,
3-(3,4-dichlorobenzylamino)-2(S)-hydroxypropyl(diethoxymethyl)phosphinic acid, and
3-(p-chlorobenzylamino)propyl(cyclohexylmethyl)-phosphinic acid
and their pharmaceutically acceptable salts, as such.

The process for the preparation of the novel araliphatically N-substituted aminoalkanephosphinic acids of formula I provided in accordance with the invention comprises, in a compound of formula II

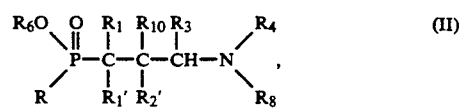

wherein $R_1$, $R_1'$, $R_2'$ and $R_3$ are hydrogen, $R_6$ is a hydroxy-protecting group, $R_8$ is a group $R_5$ or an amino-protecting group and $R_{10}$ is hydrogen or protected hydroxy, and R, $R_1$, $R_4$ and $R_5$ are as defined above, or in a salt thereof, freeing the hydroxy groups by replacing the hydroxy-protecting group $R_6$ by hydrogen and, where appropriate, removing the amino-protecting group $R_8$ and, where appropriate, freeing the hydroxy groups $R_2$ from the protected hydroxy group $R_{10}$, and, if desired, converting a resulting compound into a different compound of formula I, separating a mixture of isomers obtainable in accordance with the process into the components and separating the preferred isomer, and/or converting a free compound obtainable in accordance with the process into a salt or converting a salt obtainable in accordance with the process into the corresponding free compound.

Protected hydroxy groups $R_6O$ are, for example, etherified hydroxy groups, preferably hydroxy groups etherified by an aliphatic, cycloaliphatic, araliphatic or aromatic alcohol or by a silanol, such as, especially, lower alkoxy, lower alkenyloxy, phenyloxy or phenylalkoxy, such as benzyloxy, each of which is unsubstituted or substituted, for example, by lower alkyl, lower alkoxy, halogen and/or by nitro, or tri-lower alkylsilyloxy, such as trimethylsilyloxy, tributylsilyloxy or tert-butyl(dimethyl)silyloxy.

The protecting group $R_6$ in the compounds of formula II can be replaced by hydrogen by treatment with a suitable basic or acidic agent, such as an alkali metal hydroxide, for example sodium hydroxide or lithium hydroxide, an alkali metal halide, especially an alkali metal bromide or iodide, such as lithium bromide or sodium iodide, thiourea, an alkali metal thiophenolate, such as sodium thiophenolate, or a protonic or Lewis acid, such as a mineral acid, for example hydrochloric acid, or a tri-lower alkylhalosilane, for example trimethylchlorosilane. The exchange reaction can be carried out in the absence or presence of a solvent and, if necessary, with heating or with cooling, in a closed vessel and/or under an inert gas atmosphere.

The replacement of the $R_6$ protecting group, for example a silyl or alkyl group, in compounds of formula II by hydrogen can, however, also be effected by treatment with an acid under hydrolytic conditions, especially with a mineral acid, such as a hydrohalic acid, for example hydrochloric acid, which is used in dilute or concentrated aqueous form, or by treatment with an organic silyl halide, such as trimethyliodosilane or trimethylbromosilane, and, if necessary, subsequent hydrolysis. The reaction is preferably carried out at elevated temperature, for example by keeping the reaction mixture under reflux, and, optionally, using an organic diluent, in a closed vessel and/or in an inert gas atmosphere. The type and manner of the replacement of the protecting group $R_6$ is dependent, for example, upon the substituent R which is contained in the compound of formula II and must be retained when the compound II is converted into a compound of formula I. The said conversion may be carried out, for example, as described in the Preparation Examples.

Amino-protecting groups $R_8$ in compounds of formula II can be removed by known processes which are selected according to the type of amino-protecting group, for example by solvolytic or hydrogenolytic processes, for example hydrolysis in the presence of an acid or base, acidolysis, for example treatment with trifluoroacetic acid, treatment with hydrazine, or hydrogenolysis in the presence of a metal hydrogenation catalyst, or by any other suitable process.

Depending upon the groups involved, the exchange and the conversion can be carried out in succession or simultaneously in accordance with methods known per se.

Preferably, all the protecting groups, hydroxy-protecting groups $R_6$ or $R_{10}$ and amino-protecting groups $R_8$ are replaced by hydrogen in a single step by treatment with a tri-lower alkylsilyl halide, such as trimethylbromosilane, or with an acid, preferably a hydrohalic acid, especially hydrochloric acid, under hydrolytic conditions.

The starting materials of formula II can be prepared in various ways, for example by a) introducing into a compound of formula III

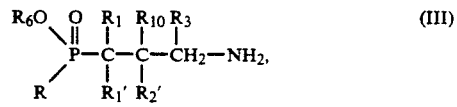

wherein $R_1$, $R_1'$, $R_2'$ and $R_3$ are hydrogen, $R_6$ is as defined above and $R_{10}$ is hydrogen or protected hydroxy, the group $R_4$ and, if desired, a radical $R_5$ other than hydrogen, or b) reacting a compound of formula IV

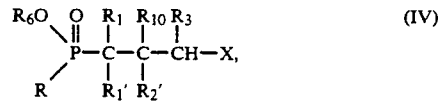

wherein $R_1$, $R_1'$, $R_2'$ and $R_3$ are hydrogen, X is a reactive esterified hydroxy group and $R_{10}$ is hydrogen or protected hydroxy, or a salt thereof, with a compound of formula

wherein $R_4$ and $R_8$ are as defined above, or c) condensing a compound of formula VI

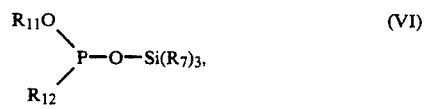

wherein $R_{11}$ is a group $R_6$ or $-Si(R_7)_3$, $R_{12}$ is a radical R protected at a hydroxy group which may be present by a group $-Si(R_7)_3$, and the radicals $R_7$ are identical or different aliphatic hydrocarbon radicals, for example lower alkyl, especially methyl and/or tert-butyl, with a compound of formula VII

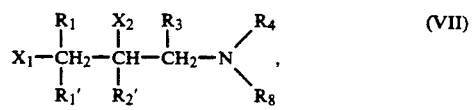

wherein $R_1$, $R_1'$, $R_2'$ and $R_3$ are hydrogen, $X_1$ is reactive esterified hydroxy and $X_2$ is hydrogen, or $X_1$ and $X_2$ together are epoxy, and $R_8$ is a group $R_5$ or an amino-protecting group, or d) reacting a compound of formula VIII

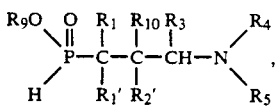

(VIII)

wherein $R_1$, $R_1'$, $R_2'$ and $R_3$ are hydrogen, $R_9$ is hydrogen or a group $R_6$ and $R_{10}$ is hydrogen or protected hydroxy, with a silylating agent and reacting the resulting silyl-activated compound of formula IX

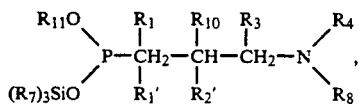

(IX)

wherein $R_8$ is a group $R_5$ other than hydrogen or is a group of the formula $-Si(R_7)_3$, $R_{11}$ is a group $R_6$ or a group $-Si(R_7)_3$ and $R_{10}$ is hydrogen or a group of the formula $-OSi(R_7)_3$, and the radicals $R_7$ are identical or different aliphatic hydrocarbon radicals, for example lower alkyl, especially methyl and/or tert-butyl, with a reactive ester of an aliphatic, cycloaliphatic, cycloaliphatic-aliphatic or araliphatic alcohol, with an aliphatic, cycloaliphatic, cycloaliphatic-aliphatic, araliphatic or heteroarylaliphatic hydrocarbon having in the $\alpha,\beta$-position an optional additional double bond, with an aliphatic, cycloaliphatic, cycloaliphatic-aliphatic, araliphatic or heteroarylaliphatic aldehyde or ketone, or with an aliphatic epoxide, or e) for the preparation of a compound of formula II wherein $R_2$ is hydroxy, reacting a compound of formula X

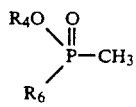

(X)

in the form of a metal salt of formula XI

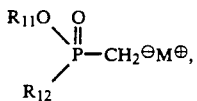

(XI)

wherein $R_{11}$ is a group $R_6$ or $-Si(R_7)_3$ and $R_{12}$ is a radical R protected at a hydroxy group which may be present by a group $-Si(R_7)_3$, in which the radicals $R_7$ are identical or different aliphatic hydrocarbon radicals, for example lower alkyl, especially methyl and/or tert-butyl, and M+ is an alkali metal cation, alkaline earth metal cation or transition metal cation, with an aldehyde of formula XII

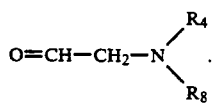

(XII)

If desired, a radical $R_5$ other than hydrogen may in each case be introduced into a compound of formula II, wherein $R_5$ is hydrogen, that is obtained initially.

The introduction of the radical $R_4$ and, optionally, $R_5$ according to process variant a) is effected in customary manner, for example by reaction with a compound of formula $X-R_2$ (IIIa) wherein X is a reactive esterified hydroxy group, especially in the presence of a basic condensation agent, such as a tertiary organic base, for example a tri-lower alkylamine, for example triethylamine, triisopropylamine or tert-butyl(dimethyl)amine, or pyridyl, or of a quaternary organic ammonium base, for example benzyl(trimethyl)ammonium hydroxide. Suitable reactive hydroxy groups are preferably hydroxy groups esterified by a mineral acid, such as halogen, especially bromine, chlorine or iodine, or groups of the formula $R_4-O-SO_4-O-$.

The radical $R_4$ can, however, also be introduced by reaction with a compound of formula $O=R_4''$ (IIIb) wherein $R_4''$ is a divalent araliphatic or heteroarylaliphatic radical the free valencies of which emanate from the same carbon atom, under reductive conditions, especially in the presence of an alkali metal borohydride, for example sodium cyanoborohydride, preferably in a lower alkanol, such as ethanol, methanol or butanol.

The condensation of the compound of formula IV with amines of formula V according to process variant b) is effected in a manner analogous to that described above for the reaction of compounds of formula III.

In compounds of formula VII according to process variant c), reactive esterified hydroxy is preferably halogen, such as bromine, iodine or chlorine, or sulfonyloxy, such as lower alkanesulfonyloxy, for example methanesulfonyloxy, or unsubstituted or substituted benzenesulfonyloxy, for example benzene-, p-toluene- or p-bromobenzene-sulfonyloxy. Amino-protecting groups are especially silyl groups, for example of the formula $-Si(R_7)_3$, such as tri-lower alkylsilyl, for example trimethylsilyl. The reaction of compounds of formula VI and reactive esters VII can be carried out in a manner known per se, preferably under the conditions of the Arbusow reaction, advantageously in a temperature range of from approximately 60° C. to approximately 180° C., for example at from approximately 120° C. to approximately 160° C. The reaction of compounds of formula VI with epoxides (VII; $X_1+X_2=$epoxy), on the other hand, is preferably carried out in the presence of a mild Lewis acid, especially zinc chloride, advantageously in an aprotic solvent.

Silylating agents that can be used in accordance with process variant d) are especially tri-lower alkylhalosilanes of formula $(R_7)_3Si-Hal$ (VIIIa) wherein $R_7$ is lower alkyl and Hal is halogen, such as chlorine, bromine or iodine, such as trimethylchlorosilane or trimethylbromosilane, or hexa-lower alkyldisilazanes of formula $(R_7)_3Si-NH-Si(R_7)_3$ (VIIIb) wherein $R_7$ is lower alkyl, such as hexamethyldisilazane. The silyl-activated intermediate is preferably a compound of formula IXa

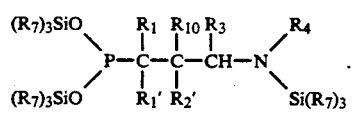

(IXa)

The reaction of the intermediate of formula IX or IXa with the component introducing the radical R is preferably carried out in the presence of a basic condensation agent, such as a tertiary organic base, for example a tri-lower alkylamine, for example triethylamine, triisopropylamine or tert-butyl(dimethyl)amine, or pyridine, or in the presence of a quaternary organic ammonium base, for example benzyl(trimethyl)ammonium hydroxide.

In starting materials of formula X for process variant e), transition metal cations are, for example, lithium, sodium or potassium cations or groups of the formula —Mg-Hal or —Zn-Hal wherein Hal is chlorine, bromine or iodine. The condensation of compounds of formulae XI and XII is effected in the manner customary for such organometal reactions.

The introduction of a radical $R_5$ other than hydrogen is effected in customary manner, especially as indicated under process variant a).

Resulting salts can be converted into the free compounds in a manner known per se, for example by treatment with a base, such as an alkali metal hydroxide, a metal carbonate or hydrogen carbonate or ammonia, or another salt-forming base mentioned at the beginning, or with an acid, such as a mineral acid, for example hydrochloric acid, or another salt-forming acid mentioned at the beginning.

Resulting salts can be converted into different salts in a manner known per se; acid addition salts, for example, by treatment with a suitable metal salt, such as a sodium, barium or silver salt, of a different acid in a suitable solvent in which an inorganic salt that forms is insoluble and is therefore eliminated from the reaction equilibrium; and base salts by freeing the free acid and forming a salt again.

The compounds of formula I, including their salts, may also be obtained in the form of hydrates or include the solvent used for crystallisation.

In view of the close relationship between the novel compounds in free form and in the form of their salts, hereinbefore and hereinafter any reference to the free compounds or their salts should be understood as including the corresponding salts or free compounds, as appropriate and expedient.

Resulting diastereoisomeric mixtures and mixtures of racemates can be separated into the pure diastereoisomers or racemates in known manner on the basis of the physico-chemical differences between the constituents, for example by means of chromatography and/or fractional crystallisation.

Furthermore, resulting racemates can be separated into the optical antipodes by known methods, for example by recrystallisation from an optically active solvent, with the aid of microorganisms, or by reaction of the resulting diastereoisomeric mixture or racemate with an optically active auxiliary compound, for example, according to the acid, basic or functionally modifiable groups contained in compounds of formula I, with an optically active acid, base or an optically active alcohol, to form mixtures of diastereoisomeric salts or functional derivatives, such as esters, and separation thereof into the diastereoisomers from which the desired enantiomer can be freed in the customary manner. Suitable bases, acids and alcohols are, for example, optically active alkaloid bases, such as strychnine, cinchonine or brucine, or D- or L-(1-phenyl)ethylamine, 3-pipecoline, ephedrine, amphetamine and similar synthetically obtainable bases, optically active carboxylic or sulfonic acids, such as quinic acid or D- or L-tartaric acid, D- or L-di-o-toluyltartaric acid, D- or L-malic acid, D- or L-mandelic acid or D- or L-camphorsulfonic acid, and optically active alcohols, such as borneol or D- or L-(1-phenyl)ethanol.

The invention relates also to those forms of the process in which a compound obtainable as intermediate at any stage of the process is used as starting material and the remaining steps are carried out, or in which a starting material is used in the form of a salt or, especially, is formed under the reaction conditions.

The invention relates also to the novel starting materials developed specifically for the preparation of the compounds according to the invention, especially to those starting materials resulting in the compounds of formula I that were described at the beginning as being preferred, to processes for the preparation thereof and to their use as intermediates.

Compounds of formula I wherein $R_4$ and $R_5$ are hydrogen, which are also used as starting materials for process variant a), can be prepared, for example, by reacting a compound of formula XIII protected at the hydroxy group which may be present

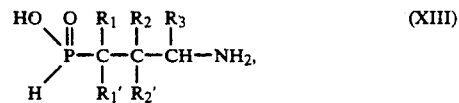

wherein $R_1$, $R_1'$, $R_2$, $R_2'$ and $R_3$ are as defined above, with a tri-lower alkylhalosilane, such as trimethylchlorosilane, or with a hexa-lower alkyldisilazane, for example hexamethyldisilazane, and condensing the resulting silyl-activated compound of formula XIV

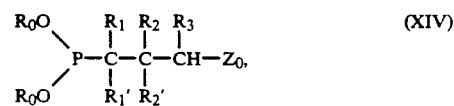

wherein $R_0$ is a tri-lower alkylsilyl group, such as trimethylsilyl, and $Z_0$ is N,N-di(tri-lower alkylsilyl)amino, with a corresponding aliphatic, cycloaliphatic-aliphatic or araliphatic halide of formula R-Hal (XV; Hal=halogen) or an aliphatic, cycloaliphatic-aliphatic or araliphatic aldehyde of formula R'—CH=O (XVI) wherein R' is a radical R reduced by a terminal $CH_2$ group, to form the corresponding compound of formula XVII

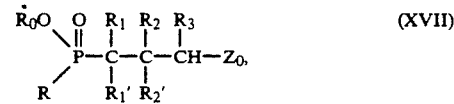

wherein R is an aliphatic, cycloaliphatic-aliphatic or araliphatic radical or a group of the formula R—CH-(OH)—, or reacting the compound of formula XIV with an aliphatic, cycloaliphatic, cycloaliphatic-aliphatic or araliphatic ketone of formula R''—C(-=O)—R''' (XVIII), wherein R'' is an aliphatic, cycloaliphatic or aromatic radical and R''' is an aliphatic radical, to form the corresponding compound of formula V wherein R is a radical of the formula R''—C(R'''-)(OH)—, or with a corresponding aliphatic, cycloaliphatic-aliphatic or araliphatic epoxide or a corresponding aliphatic, cycloaliphatic, cycloaliphatic-aliphatic or araliphatic compound having at least one additional olefinic double bond, and in each case working up the primary product, for example of formula XVII, by hydrolysis.

Compounds of formula I wherein $R_1$ and $R_1'$ are hydrogen, $R_2$ is an aromatic radical, $R_2'$ is hydroxy and $R_3$, $R_4$ and $R_5$ are hydrogen, which are also used as starting materials for process variant a), can be prepared especially by reacting compounds of formulae XIX and XX

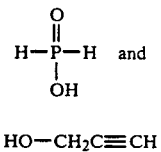  (XIX)

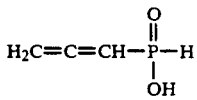  (XX)

in an araliphatic solvent, such as toluene, to form the corresponding compound of formula XXI

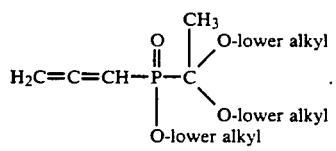  (XXI)

and converting the latter by reaction first with a haloformic acid lower alkyl ester, such as chloroformic acid ethyl ester, in the presence of a tri-lower alkylamine, such as triethylamine, and then with an orthoacetic acid tri-lower alkyl ester, such as orthoacetic acid triethyl ester, in the presence of a Lewis acid, such as boron trifluoride, into a compound of formula XXII

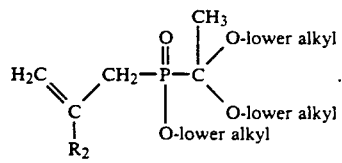  (XXII)

The compound of formula XXII is then reacted in the presence of the 1:1 complex of copper(I) bromide and dimethyl sulfide with a compound of formula $R_2$-M (XXIII), wherein M is a metal radical, especially a halomagnesium group, to form the corresponding compound of formula XXIV

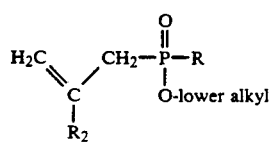  (XXIV)

In a one-pot reaction the P-protecting groups (lower alkyl radicals) can then be removed by treatment with trimethylchlorosilane in dichloromethane/ethanol and the group R can be introduced by reaction with a compound of formula XV, XVI or XVIII, with an aliphatic, cycloaliphatic-aliphatic or araliphatic epoxide or a corresponding aliphatic, cycloaliphatic, cycloaliphatic-aliphatic or araliphatic unsaturated compound, as described for the reaction thereof with compounds of formula XIV. The resulting compound of formula XXV

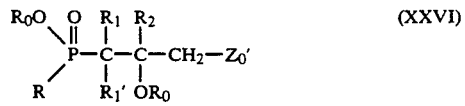  (XXV)

is then reacted in an acetonitrile/tert-butanol/water mixture in the presence of silver nitrate and osmium tetroxide with a reagent obtained by reaction of tert-butylurethane with tert-butoxy chloride in a lower alkanol in the presence of sodium hydroxide. The primary product so obtained is then converted by means of trimethylbromosilane in dichloromethane and treatment with aqueous methanol and then with propylene oxide into the desired compound of formula XXVI $$\begin{array}{c} R_0O\phantom{xx}O\phantom{xx}R_1\phantom{x}R_2 \\ \diagdown\phantom{x}\|\phantom{xx}|\phantom{xx}| \\ P-C-C-CH_2-Z_0{'} \\ \diagup\phantom{xx}|\phantom{xx}| \\ R\phantom{xxxx}R_1{'}\phantom{x}OR_0 \end{array}$$  (XXVI)

wherein $R_0$ is a silyl group and $Z_0{'}$ is tert-butoxycarbonyl. Treatment with aqueous methanol and then with propylene oxide yields the desired compound of formula I.

The novel compounds of formula I can be used, for example, in the form of pharmaceutical compositions that comprise a therapeutically effective amount of the active ingredient, optionally together with inorganic or organic, solid or liquid pharmaceutically acceptable carriers that are suitable for enteral, for example oral, or parenteral administration.

Pharmaceutical compositions that comprise known $GABA_B$-antagonists, for example known compounds of formula I, are intended especially as anti-epileptics.

The pharmaceutical compositions according to the invention are pharmaceutical compositions in unit dose form that comprise a therapeutically effective amount of the active ingredient on its own or together with a pharmaceutically acceptable carrier, especially inorganic or organic, solid or liquid pharmaceutically acceptable carriers, so that they are suitable for enteral, such as oral, and also rectal, and parenteral administration to warm-blooded animals.

The pharmaceutical compositions, such as anti-epileptics, provided according to the invention comprise, for example, from approximately 10% to approximately 80%, preferably from approximately 20% to approximately 60%, active ingredient. Pharmaceutical compositions according to the invention for enteral or parenteral administration are, for example, pharmaceutical compositions in unit dose form, such as dragées, tablets, capsules or suppositories, and also injection or infusion solutions, preferably in ampoules. The compositions are prepared in a manner known per se, for example by means of conventional mixing, granulating, confectioning, dissolving or lyophilising processes. For example, pharmaceutical compositions for oral administration can be obtained by combining the active ingredient with solid carriers, if desired granulating a resulting mixture and, if desired or necessary, processing the mixture or granules, after the addition of suitable excipients, to form tablets or dragée cores.

Suitable carriers are especially fillers, such as sugars, for example lactose, saccharose, mannitol or sorbitol, cellulose preparations and/or calcium phosphates, for example tricalcium phosphate or calcium hydrogen phosphate, and binders, such as starch pastes using, for example, corn, wheat, rice or potato starch, gelatin, tragacanth, methylcellulose and/or polyvinylpyrrolidone, if desired, disintegrators, such as the above-mentioned starches, also carboxymethyl starch, crosslinked polyvinylpyrrolidone, agar, alginic acid or a salt thereof, such as sodium alginate. Excipients are especially flow conditioners and lubricants, for example silicic acid, talc, stearic acid or salts thereof, such as magnesium or calcium stearate, and/or polyethylene glycol. Dragée cores are provided with suitable, optionally enteric, coatings, there being used, inter alia, concentrated sugar solutions which may comprise gum arabic, talc, polyvinylpyrrolidone, polyethylene glycol and/or titanium dioxide, or coating solutions in suitable organic solvents or solvent mixtures, or, for the preparation of enteric coatings, solutions of suitable cellulose preparations, such as acetylcellulose phthalate or hydroxypropylmethylcellulose phthalate. Dyes or pigments may be added to the tablets or dragée coatings, for example for identification purposes or to indicate different doses of active ingredient.

Other orally administrable pharmaceutical compositions are dry-filled capsules consisting of gelatin, and also soft sealed capsules consisting of gelatin and a plasticiser, such as glycerol or sorbitol. The dry-filled capsules may contain the active ingredient in the form of granules, for example in admixture with fillers, such as lactose, binders, such as starches, and/or glidants, such as talc or magnesium stearate, and, if desired, stabilisers. In soft capsules, the active ingredient is preferably dissolved or suspended in suitable liquids, such as fatty oils, paraffin oil or liquid polyethylene glycol, to which stabilisers may also be added.

Suitable rectally administrable pharmaceutical compositions are, for example, suppositories that consist of a combination of the active ingredient with a suppository base. Suitable suppository bases are, for example, natural or synthetic triglycerides, paraffin hydrocarbons, polyethylene glycol or higher alkanols. There may also be used gelatin rectal capsules, which contain a combination of the active ingredient with a base material. Suitable base materials are, for example, liquid triglycerides, polyethylene glycols or paraffin hydrocarbons.

For parenteral administration there are suitable, especially, aqueous solutions of an active ingredient in water-soluble form, for example in the form of a water-soluble salt, and also suspensions of the active ingredient, such as corresponding oily injection suspensions, there being used suitable lipophilic solvents or vehicles, such as fatty oils, for example sesame oil, or synthetic fatty acid esters, for example ethyl oleate or triglycerides, or aqueous injection suspensions that comprise viscosity-increasing substances, for example sodium carboxymethylcellulose, sorbitol and/or dextran, and, if desired, also stabilisers.

The pharmaceutical compositions can be sterilised and, if desired, comprise further pharmacologically active substances and/or excipients, for example preservatives, stabilisers, wetting agents and/or emulsifiers, solubilisers, salts for regulating the osmotic pressure and/or buffers.

The dosage can depend upon various factors, such as the mode of administration, the species, age and/or individual condition. The daily doses are, in the case of oral administration, from approximately 5 to approximately 60 mg/kg, especially from 10 to approximately 40 mg/kg, and in the case of warm-blooded animals having a body weight of approximately 40 kg, they are preferably from approximately 200 mg to approximately 2400 mg, especially from approximately 400 to approximately 1600 mg, which is advantageously divided into from 2 to 6, for example 3 or 4, single doses.

The following Examples illustrate the invention; temperatures are given in degrees Celsius and pressures in mbar.

PREPARATION EXAMPLE 1

A solution of 0.36 g of lithium hydroxide monohydrate in 7 ml of water is added to a solution of 1.61 g of 3-(p-chlorobenzylamino)propyl(diethoxymethyl)phosphinic acid ethyl ester in 3 ml of ethanol, and the mixture is heated at 60° for 24 hours. The mixture is then cooled to room temperature and the solvent is removed under reduced pressure. The evaporation residue is taken up in water and neutralised with phosphoric acid. A white precipitate forms and is filtered off, and the filtrate is concentrated to dryness by evaporation. The white residue is dried under reduced pressure and crystallised from toluene/diethyl ether. Filtration with suction and drying yield 3-(p-chlorobenzylamino)propyl(diethoxymethyl)phosphinic acid having a melting point of 177°–179°.

The starting material can be prepared, for example, as follows:

1.41 g of p-chlorobenzaldehyde are added to a solution of 2.53 g of 3-aminopropyl(diethoxymethyl)phosphinic acid ethyl ester in 10 ml of anhydrous methanol, and the resulting clear solution is stirred at room temperature for 30 minutes. There are then added first 0.6 g of glacial acetic acid and then, dropwise, 0.21 g of sodium cyanoborohydride in solution in 5 ml of methanol. An exothermic reaction begins. The mixture is stirred at 20° for 3 hours and adjusted to pH 8, and the solvent is removed. The residue is dissolved in dichloromethane and washed with water. The organic phase is separated off, dried over sodium sulfate and concentrated to dryness by evaporation. The oil that remains is purified by chromatography on silica gel, yielding 3-(p-chlorobenzylamino)propyl(diethoxymethyl)phosphinic acid ethyl ester in the form of a yellowish oil.

PREPARATION EXAMPLE 2

A solution of 1.80 g of (2S)-3-(p-chlorobenzylamino)-2-hydroxypropyl(benzyl)phosphinic acid ethyl ester in 30 ml of semi-concentrated hydrochloric acid is heated under reflux, a whitish suspension forming after 30 minutes. The mixture is heated under reflux for a further 20 hours and cooled to 0°, and the solid portion is filtered off, washed with water and dried under reduced pressure at 60°. Recrystallisation from aqueous methanol and drying yield 3-(p-chlorobenzylamino)-2-(2S)-hydroxypropyl(benzyl)phosphinic acid hydrochloride having a melting point of 211.5°–212°.

The starting material can be prepared as follows:

A solution of diethoxymethylphosphinic acid ethyl ester is added within a period of 90 minutes, under argon, to a suspension of 13.2 g of 99% sodium hydride in 500 ml of tetrahydrofuran, the temperature being maintained at 20°. The reaction is exothermic and is accompanied by the evolution of gas. The mixture is then stirred for 90 minutes, and 85.5 g of benzyl bromide are then added within a period of 20 minutes. The mixture is then stirred at room temperature for 24 hours and cooled to 0°, and 100 ml of water are added carefully. The organic solvents are removed under reduced pressure and the residue is partitioned between water and dichloromethane. The organic phase is separated off, washed with water, dried over sodium sulfate and concentrated by evaporation. Distillation of the residue under reduced pressure yields diethoxymethyl(benzyl)phosphinic acid ethyl ester having a boiling point of 103°–110° ($3 \times 10^{-4}$ bar).

A suspension of 128 g of diethoxymethyl(benzyl)-phosphinic acid ethyl ester in 400 ml of hydrochloric acid is heated under reflux for 20 hours, cooled to room temperature, washed with diethyl ether/hexane (1:1) and concentrated to dryness by evaporation. The residue is taken up in dichloromethane, dried over sodium sulfate and again concentrated by evaporation. The viscous benzylphosphinic acid that remains is then dried under a high vacuum.

13.34 g of benzylphosphinic acid are dissolved in 150 ml of dichloromethane, the solution is cooled to 5°, and 8.64 g of triethylamine are added dropwise. An exothermic reaction takes place. The mixture is cooled to 5° again, and 9.3 g of chloroformic acid ethyl ester are added dropwise within a period of 30 minutes. A precipitate forms in an exothermic reaction with the evolution of gas. The mixture is allowed to warm to room temperature and is then stirred at room temperature for 3 hours, taken up in dichloromethane and washed with water, and the organic solvent is removed. The crude product is distilled under a high vacuum, yielding benzylphosphinic acid ethyl ester having a boiling point of 96°-100° ($5 \times 10^{-6}$ bar).

26.7 g of benzylphosphinic acid ethyl ester and 16.0 g of triethylamine are dissolved in 250 ml of tetrahydrofuran, 17.33 g of trimethylchlorosilane are added, and the mixture is stirred overnight at room temperature. The white precipitate that has formed is filtered off under argon and the filtrate is concentrated by evaporation under reduced pressure. 14.71 g of (R)-epichlorohydrin and 2.5 g of zinc chloride are added to the residue. When the exothermic reaction has subsided, the mixture is heated under reflux for 7.5 hours at 60°. The mixture is allowed to cool to room temperature, diluted with dichloromethane and washed with water. The organic phase is separated off, dried over sodium sulfate and concentrated by evaporation. The oily residue is taken up with 1% methanolic acetic acid, left to stand at room temperature for 20 hours and concentrated by evaporation. The residue is purified by chromatography on silica gel, yielding (2R)-3-chloro-2-hydroxypropyl(benzyl)phosphinic acid ethyl ester; $^1$H-NMR spectrum (in CDCl$_3$): $\delta = 7.3$ (5H,m); 2.19-3.92 (3H,m); 3.6-3.42 (2H,m); 3.21 (2H,d; J=15.0 Hz); 2.16-1.81 (2H,m); 1.30 (3H,t); $^{31}$P-NMR spectrum (in CDCl$_3$): $\delta = 52.1$.

A mixture of 2.76 g of (2R)-3-chloro-2-hydroxypropyl(benzyl)phosphinic acid ethyl ester, 3.54 g of p-chlorobenzylamine, 3.25 g of N-ethyl-N,N-diisopropylamine and 20 ml of ethanol is heated under reflux for 48 hours. Removal of the solvent and chromatography yield (2S)-3-(p-chlorobenzylamino)-2-hydroxypropyl(benzyl)phosphinic acid ethyl ester; $^1$H-NMR spectrum (in CDCl$_3$): $\delta = 7.4$-7.17 (9H,m); 4.14-3.83 (3H,m); 3.71 (2H,ABq); 3.20 (2H,d); 2.6-2.5 (2H,m); 1.96-1.62 (2H,m); 1.25 (3H,t); $^{31}$P-NMR spectrum (in CDCl$_3$): $\delta = 53.9$; 52.7.

PREPARATION EXAMPLE 3

A solution of 1.86 g of 3-(p-chlorobenzylamino)-propyl(n-butyl)phosphinic acid ethyl ester in 30 ml of semi-concentrated hyrochloric acid is heated under reflux overnight, a clear solution forming after only 10 minutes. The solution is then cooled to 0°, whereupon a white precipitate forms. The precipitate is filtered off, washed with water and dried under reduced pressure at 60°. Recrystallisation from water and drying yield 3-(p-chlorobenzylamino)propyl(n-butyl)phosphinic acid hydrochloride having a melting point of 212°-214°.

The starting material can be prepared as follows:

24 g of a 55% suspension of sodium hydride in mineral oil are washed under argon with hexane and then taken up in 100 ml of tetrahydrofuran. The mixture is cooled to 0° and a solution of 104.4 g of diethoxymethylphosphinic acid ethyl ester in 100 ml of tetrahydrofuran is added dropwise under argon, the temperature being maintained at 20°. The reaction is exothermic and is accompanied by the evolution of gas. The mixture is then stirred for 90 minutes and then 209.7 g of n-butyl bromide are added at 20°. The mixture is then stirred for 2.5 hours at room temperature and cooled to 0°, and 100 ml of water are added carefully. The organic solvents are removed under reduced pressure, and the residue is partitioned between water and dichloromethane. The organic phase is separated off, washed with water, dried over sodium sulfate and concentrated by evaporation. Distillation of the residue under reduced pressure yields diethoxymethyl(n-butyl)phosphinic acid ethyl ester having a boiling point of 71.5°-74° ($10^{-6}$ bar).

A solution of 109 g of diethoxymethyl(n-butyl)phosphinic acid ethyl ester in 160 ml of 4N hydrochloric acid is heated under reflux for 24 hours, cooled to room temperature, washed with diethyl ether and concentrated to dryness by evaporation. The residue is subjected to azeotropic distillation with ethanol and concentrated by evaporation again. The n-butylphosphinic acid that remains is dried under a high vacuum at 50° for 20 hours, yielding an oil; $^1$H-NMR spectrum (in CDCl$_3$): $\delta = 11.13$ (1H,s); 7.11 (1H,dt; J=52.0 and 0.2 Hz); 1.77 (2H,m); 1.58 (2H,m); 0.3 (3H,t).

51 g of n-butylphosphinic acid are dissolved in 200 ml of dichloromethane, the solution is cooled to 10°, and 42.3 g of triethylamine are added dropwise. An exothermic reaction takes place. The mixture is cooled to 10° again and 45.3 g of chloroformic acid ethyl ester are added dropwise within a period of 75 minutes. A precipitate forms in an exothermic reaction with the evolution of gas. A further 200 ml of dichloromethane are then added and the mixture is allowed to warm to room temperature and is then stirred for 2 hours at room temperature, washed with water and dried over sodium sulfate, and the organic solvent is removed. The crude product is distilled under a high vacuum, yielding n-butyl-phosphonic acid ethyl ester having a boiling point of 95° ($5 \times 10^{-5}$ bar).

15.0 g of n-butylphosphonic acid ethyl ester and 5.3 g of acrylonitrile are dissolved under argon in 25 ml of ethanol. The solution is cooled to 10°, and a solution of 1.15 g of sodium in 50 ml of ethanol is added dropwise, whereupon an exothermic reaction takes place. The mixture is then heated under reflux for one hour and cooled to room temperature, and 3.3 g of glacial acetic acid are added. The solvent is removed and the residue is taken up in dichloromethane. The resulting solution is washed with water, dried over sodium sulfate and concentrated by evaporation. The oil that remains is distilled, yielding 2-cyanoethyl(n-butyl)phosphinic acid ethyl ester having a boiling point of 120° ($10^{-1}$ bar).

16.46 g of 2-cyanoethyl(n-butyl)phosphinic acid ethyl ester are dissolved in 165 ml of ethanol, the solution is mixed with 16.5 g of ammonia and 3.0 g of Raney nickel, and the mixture is hydrogenated for 2 hours at 70°-75° under an initial pressure of 100 bar. The mixture is allowed to cool to room temperature, the catalyst is filtered off, the solvent is removed and the residue is distilled, yielding 3-aminopropyl(n-butyl)phosphinic acid ethyl ester having a boiling point of 100° (10⁻⁵ bar).

4.14 g of 3-aminopropyl(n-butyl)phosphinic acid ethyl ester are mixed with 2.51 g of p-chlorobenzaldehyde, and first 1.2 g of glacial acetic acid and then a solution of 0.42 g of sodium cyanoborohydride in 5 ml of methanol are added, whereupon an exothermic reaction takes place. The mixture is then stirred at room temperature for 2.5 hours and adjusted to pH 8, and the volatile constituents are removed under reduced pressure. The residue is dissolved in dichloromethane, washed with water, dried over sodium sulfate and concentrated by evaporation. The residue is purified by chromatography on silica gel, yielding 3-(p-chlorobenzylamino)propy(n-butyl)phosphinic acid ethyl ester; $^1$H-NMR spectrum (in CDCl$_3$): $\delta$=7.30-7.32 (4H,m); 4.02 (2H,q); 3.74 (2H,s); 2.67 (2H,t); 2.5-2.22 (1H,S); 1.79-1.64 (6H,m); 1.53 (2H,m); 1.42 (2H,m); 1.31 (3H,t); 0.81 (3H,t); $^{31}$P-NMR spectrum (in CDCl$_3$): $\delta$=58.16.

PREPARATION EXAMPLE 4

In a manner analogous to that described in Preparation Example 1, 3-(p-chlorobenzylamino)propyl(cyclohexylmethyl)phosphinic acid having a melting point of 218°-219° can be prepared starting from 3-aminopropyl(cyclohexylmethyl)phosphonic acid ethyl ester and p-chlorobenzaldehyde.

PREPARATION EXAMPLE 5

In a manner analogous to that described in Preparation Example 2, 3-(p-chlorobenzylamino)-2(2R)-hydroxypropyl(benzyl)phosphinic acid having a melting point of 218°-222° can be prepared starting from benzylphosphinic acid ethyl ester, (S)-epichlorohydrin and p-chlorobenzaldehyde.

PREPARATION EXAMPLE 6

In a manner analogous to that described in Preparation Example 1, 3-(3,4-dichlorbenzylamino)propyl(diethoxymethyl)phosphonic acid having a melting point of 175°-176° can be prepared starting from 3-aminopropyl(diethoxymethyl)phosphinic acid ethyl ester and 3,4-dichlorobenzaldehyde.

PREPARATION EXAMPLE 7

In a manner analogous to that described in Preparation Example 1, 3-[1-(p-chlorophenyl)ethylamino]-propyl(diethoxymethyl)phosphinic acid, hygroscopic crystals, $^{31}$P-NMR (CD$_3$OD): $\delta$=47.1 ppm, can be prepared starting from 3-aminopropyl(diethoxymethyl)phosphinic acid ethyl ester and p-chloroacetophenone.

PREPARATION EXAMPLE 8

In a manner analogous to that described in Preparation Example 1, 3-(naphth-1-ylmethylamino)propyl(diethoxymethyl)phosphinic acid having a melting point of 222°-225° can be prepared starting from 3-aminopropyl(diethoxymethyl)phosphinic acid ethyl ester and 1-formylnaphthalene.

PREPARATION EXAMPLE 9

In a manner analogous to that described in Preparation Example 3, 3-(3,4-dichlorobenzylamino)propyl(cyclohexylmethyl)phosphonic acid hydrochloride having a melting point of 115°-226° can be prepared starting from 3-aminopropyl(cyclohexylmethyl)phosphonic acid ethyl ester and 3,4-dichlorobenzaldehyde.

PREPARATION EXAMPLE 10

In a manner analogous to that described in Preparation Example 3, 3-(pyrid-2-ylmethylamino)-2(S)-hydroxypropyl(benzyl)phosphonic acid hydrochloride, $|\alpha|_{20}{}^D$=10.2±0.2 (c=1% in CH$_3$OH), can be prepared starting from 3-chloro-2(R)-hydroxypropyl(benzyl)phosphinic acid ethyl ester and 2-aminomethylpyridine.

PREPARATION EXAMPLE 11

In a manner analogous to that described in Preparation Example 2, 3-(p-chlorobenzylaminoyl)-2(S)-hydroxypropyl(cyclohexylmethyl)phosphinic acid hydrochloride having a melting point of 206°-210° can be prepared starting from 3-chloro-2(R)-hydroxypropyl(cyclohexylmethyl)phosphinic acid ethyl ester and p-chlorobenzylamine.

PREPARATION EXAMPLE 12

In a manner analogous to that described in Preparation Example 2,3-(3,4-dichlorobenzylaminoyl)2-(S)-hydroxypropyl(benzyl)phosphinic acid hydrochloride having a melting point of 186°-187° can be prepared starting from 3-chloro-2(R)-hydroxypropyl(benzyl)-phosphinic acid ethyl ester and 3,4-dichlorobenzylamine.

PREPARATION EXAMPLE 13

In a manner analogous to that described in Preparation Example 1,3-(p-fluorobenzylamino)propyl(diethoxymethyl)phosphinic acid having a melting point of 128°-129° can be prepared starting from 3-aminopropyl(diethoxymethyl)phosphinic acid ethyl ester and p-fluorobenzaldehyde.

PREPARATION EXAMPLE 14

In a manner analogous to that described in Preparation Example 1,3-(4-chloro-3-trifluoromethylbenzylamino)propyl(diethoxymethyl)phosphinic acid having a melting point of 138°-139° can be prepared starting from 3-aminopropyl(diethoxymethyl)phosphinic acid ethyl ester and 4-chloro-3-trifluoromethylbenzaldehyde.

PREPARATION EXAMPLE 15

In a manner analogous to that described in Preparation Example 1,3-(m-chlorobenzylamino)propyl(diethoxymethyl)phosphinic acid having a melting point of 158°-160° can be prepared starting from 3-aminopropyl(diethoxymethyl)phosphinic acid ethyl ester and m-chlorobenzaldehyde.

PREPARATION EXAMPLE 16

In a manner analogous to that described in Preparation Example 2,3-(3,4-dichlorobenzylamino)-2-(S)-hydroxypropyl(cyclohexymethyl)phosphinic acid hydrochloride having a melting point of 193°-196° can be prepared starting from 3-chloro-2(R)-hydroxypropyl(cyclohexylmethyl)phosphinic acid ethyl ester and 3,4-dichlorobenzylamine.

PREPARATION EXAMPLE 17

In a manner analogous to that described in Preparation Example 1,3-[1-(3,4-dichlorophenyl)ethylamino]-propyl(diethoxymethyl)phosphinic acid having a melting point of 85°-90° can be prepared starting from 3- aminopropyl(diethoxymethyl)phosphinic acid ethyl ester and 3,4-dichloroacetophenone.

PREPARATION EXAMPLE 18

In a manner analogous to that described in Preparation Example 2,3-[1-(p-chlorophenyl)aminoethyl]-2(S)-hydroxypropyl(benzyl)phosphinic acid hydrochloride having a melting point of 93°-95° can be prepared starting from 3-chloro-2(R)-hydroxypropyl(benzyl)phosphinic acid ethyl ester and 1-(p-chlorophenyl)ethylamine.

PREPARATION EXAMPLE 19

In a manner analogous to that described in Preparation Example 1,3-(p-iodobenzylamino)propyl(diethoxymethyl)phosphinic acid having a melting point of 108°-110° can be prepared starting from 3-aminopropyl(diethoxymethyl)phosphinic acid ethyl ester and p-iodobenzaldehyde.

PREPARATION EXAMPLE 20

In a manner analogous to that described in Preparation Example 1,3-(2,4-dichlorobenzylamino)propyl(diethoxymethyl)phosphinic acid having a melting point of 173°-175° can be prepared starting from 3-aminopropyl(diethoxymethyl)phosphinic acid ethyl ester and 2,4-dichlorobenzaldehyde.

PREPARATION EXAMPLE 21

In a manner analogous to that described in Preparation Example 1,3-(o-chlorobenzylamino)propyl(diethoxymethyl)phosphinic acid having a melting point of 162°-163° can be prepared starting from 3-aminopropyl(diethoxymethyl)phosphinic acid ethyl ester and o-chlorobenzaldehyde.

PREPARATION EXAMPLE 22

In a manner analogous to that described in Preparation Example 1,3-(3,4-dichlorobenzylamino)propyl(cyclopropylmethyl)phosphinic acid having a melting point of 214°-215° can be prepared starting from 3-aminopropyl(cyclopropylmethyl)phosphinic acid ethyl ester and 3,4-dichlorobenzaldehyde.

PREPARATION EXAMPLE 23

0.38 g of trimethylbromosilane is added to a solution of 0.41 g of 3-(p-chlorobenzylamino)propyl(tetrahydrofuran-2-yl)phosphinic acid ethyl ester, the mixture is stirred at room temperature for 24 hours, and the volatile constituents are removed under reduced pressure. The oil that remains is taken up in 99% methanol, stirred for 30 minutes at room temperature and again concentrated by evaporation under reduced pressure. Recrystallisation of the solid yellowish residue yields 3-(p-chlorobenzylamino)propyl(tetrahydrofuran-2-yl)phosphinic acid hydrochloride having a melting point of 212°-213°; $^1$H-NMR spectrum (in CD$_3$OD): $\delta$=7.5 (4H,m), 4.21 (2H,s), 4.03 (1H, ABq), 3.84 (2H, t,d), 3.17 (2H,t), 2.30-1.83 (8H,m); $^{31}$P-NMR spectrum (in CD$_3$OD): $\delta$=49.4.

PREPARATION EXAMPLE 24

0.43 g of lithium hydroxide monohydrate in 6 ml of water is added to a solution of 2.0 g of 3-[N-(p-chlorobenzyl)-N-methylamino]propyl(diethoxymethyl)phosphinic acid ethyl ester in 5.5 ml of ethanol, and the mixture is heated at 60° for 25 hours. The reaction mixture is cooled to room temperature, the solvent is removed under reduced pressure, and the evaporation residue is taken up in water and neutralised with phosphoric acid. The suspension formed is concentrated to dryness by evaporation, and the residue is taken up in hot methanol, filtered and concentrated by evaporation again. Crystallisation of the residue from propanol yields 3-[N-(p-chlorobenzyl)-N-methylamino]propyl(diethoxymethyl)phosphinic acid having a melting point of 170°-171.5°.

The starting material can be prepared, for example, as follows:

2.5 g of 3-(p-chlorobenzylamino)propyl(diethoxymethyl)phosphinic acid ethyl ester are dissolved in 10 ml of methanol, 0.36 g (0.53 ml) of a 35% aqueous formaldehyde solution is added, and the mixture is stirred at room temperature for one hour. 0.4 g of glacial acetic acid and 0.40 g of sodium cyanoborohydride are added, and the mixture is stirred at room temperature for 2 hours, concentrated by evaporation under reduced pressure, taken up in dichloromethane and washed with 5% aqueous sodium hydrogen carbonate solution. The organic phase is separated off, dried over sodium sulfate and concentrated by evaporation under reduced pressure. The oily residue is purified by chromatography on silica gel, yielding 3-(p-chlorobenzylamino)propyl(tetrahydrofuran-2-yl)phosphinic acid ethyl ester in the form of a colourless oil.

PREPARATION EXAMPLE 25

In a manner analogous to that described in Preparation Example 2 3-(p-chlorobenzylamino)-2(S)-hydroxypropyl(p-chlorbenzyl)phosphinic acid hydrochloride of m.p. 226°-228° can be manufactured.

PREPARATION EXAMPLE 26

In a manner analogous to that described in Preparation Example 2 3-(3,4-dichlorobenzylamino)-2(S)-hydroxy-propyl(p-chlorbenzyl)phosphinic acid hydrochloride can be manufactured.

PREPARATION EXAMPLE 27

In a manner analogous to that described in Preparation Example 2 3-(p-chlorobenzylamino)-2(S)-hydroxypropyl(p-methylbenzyl)phosphinic acid hydrochloride of m.p. 209°-210° can be manufactured. Dissolution in ethanol and treatment with propylenoxide yields 3-(p-chlorobenzylamino)-2(S)-hydroxy-propyl(p-methylbenzyl)phosphinic acid of m.p. 239.5-241.

PREPARATION EXAMPLE 28

In a manner analogous to that described in Preparation Example 2 3-(3,4-dichlorobenzylamino)-2(S)-hydroxy-propyl(p-methylbenzyl)phosphinic acid hydrochloride can be manufactured. Dissolution in ethanol and treatment with propylenoxide yields 3-(3,4-dichlorobenzylamino)-2(S)-hydroxy-propyl(p-methylbenzyl)phosphinic acid of m.p. 222.5°-224°

PREPARATION EXAMPLE 29

In a manner analogous to that described in Preparation Examples 1 to 24, the following may also be prepared:

3-(p-chlorobenzylamino)-2(S)-hydroxypropyl(diethoxymethyl)phosphinic acid;
3-[1-(p-chlorophenyl)ethylamino]-2(S)-hydroxypropyl(diethoxymethyl)phosphinic acid;
3-(3,4-dichlorobenzylamino)-2(S)-hydroxypropyl(diethoxymethyl)phosphinic acid;

3-[1-(3,4-dichlorophenyl)ethylamino]-2(S)-hydroxypropyl(diethoxymethyl)phosphinic acid;
3-[N-(p-chlorobenzyl)-N-methyl-amino]-2(S)-hydroxypropyl(benzyl)phosphinic acid;
3-(p-chlorobenzylamino)-2(S)-hydroxypropyl(p-methoxybenzyl)phosphinic acid;
3-(p-chlorobenzylamino)-2(S)-hydroxypropyl(3,4-dimethoxybenzyl)phosphinic acid;
3-(3,4-dichlorobenzylamino)-2(S)-hydroxypropyl(3,4-dimethoxybenzyl)phosphinic acid;
3-[2-(p-chlorophenyl)prop-2-ylamino]propyl(diethoxymethyl)phosphinic acid;
3-[2-(3,4-dichlorophenyl)prop-2-ylamino]propyl(diethoxymethyl)phosphinic acid;
3-[2-(p-chlorophenyl)prop-2-ylamino]-2(S)-hydroxypropyl(benzyl)phosphinic acid;
3-[2-(3,4-dichlorophenyl)prop-2-ylamino]-2(S)-hydroxypropyl(benzyl)phosphinic acid;
3-(3,4-dichlorobenzylamino)-2(S)-hydroxypropyl(3,4,5-trihydroxycyclohexylmethyl)phosphinic acid;
3-(4-chloro-3-methoxy-benzylamino)propyl(diethoxymethyl)phosphinic acid;
3-(4-chloro-3-methoxy-benzylamino)-2(S)-hydroxypropyl(benzyl)phosphinic acid;
3-(3-chloro-4-methoxy-benzylamino)-2(S)-hydroxypropyl(benzyl)phosphinic acid;
3-(2-phenylethylamino)propyl(diethoxymethyl)phosphinic acid;
3-(2-phenylethylamino)-2(S)-hydroxypropyl(diethoxymethyl)phosphinic acid;
3-(p-chlorobenzylamino-2(S)-hydroxypropyl(4-methoxycyclohexylmethyl)phosphinic acid;
3-(3,4-dichloro-6-iodo-benzylamino)-2(S)-hydroxypropyl(benzyl)phosphinic acid;
3-(3,4-dichloro-6-iodo-benzylamino)propyl(diethoxymethyl)phosphinic acid;
3-(4-chloro-3-iodo-benzylamino)propyl(diethoxymethyl)phosphinic acid;
3-(3-chloro-4-iodo-benzylamino)propyl(diethoxymethyl)phosphinic acid;
3-(4-chloro-3-iodo-benzylamino)-2(S)-hydroxypropyl(benzyl)phosphinic acid;
3-(3-chloro-4-iodo-benzylamino)-2(S)-hydroxypropyl(benzyl)phosphinic acid;
3-Di(p-chlorobenzyl)aminopropyl(diethoxymethyl)phosphinic acid;
3-Di(3,4-dichlorobenzyl)amino-2(S)-hydroxypropyl(benzyl)phosphinic acid;
3-(3,4-dichlorobenzyl)amino-2(S)-hydroxypropyl(cyclohex-3-enylmethyl)phosphinic acid
3-[1-(3,4-dichlorophenyl)ethylamino]-2(S)-hydroxypropyl(cyclohex-3-enylmethyl)phosphinic acid;
3-(3,4-dichlorobenzyl)amino-2(S)-hydroxypropyl(cis-4,5-dihydroxycyclohexylmethyl)phosphinic acid and
3-[1-(3,4-dichlorophenyl)ethylamino]-2(S)-hydroxypropyl(cis-4,5-dihydroxycyclohexylmethyl)phosphinic acid
and their pharmaceutically acceptable salts, for example their hydrochlorides.

FORMULATION EXAMPLE 1

Tablets, each comprising 200 mg of 3-aminopropyl(-cyclohexylmethyl)phosphinic acid or a salt, for example the hydrochloride, thereof, can be prepared as follows:

| Composition (10,000 tablets) | |
|---|---|
| active ingredient | 2000.0 g |
| lactose | 500.0 g |
| potato starch | 352.0 g |
| gelatin | 8.0 g |
| talc | 60.0 g |
| magnesium stearate | 10.0 g |
| silica (highly dispersed) | 20.0 g |
| ethanol | q.s. |

The active ingredient is mixed with the lactose and 292 g of potato starch, and the mixture is moistened with an ethanolic solution of the gelatin and granulated through a sieve. After drying, the remaining potato starch, the magnesium stearate, the talc and the silica are mixed in and the mixture is compressed to form tablets which each weigh 295.0 mg and comprise 50.0 mg of active ingredient, and which may, if desired, be provided with dividing notches for finer adaptation of the dose.

FORMULATION EXAMPLE 2

Film-coated tablets, each comprising 400 mg of 3-aminopropyl(cyclohexylmethyl)phosphinic acid or a salt, for example the hydrochloride, thereof, can be prepared as follows:

| Composition (for 1000 coated tablets) | |
|---|---|
| active ingredient | 400.0 g |
| lactose | 100.0 g |
| corn starch | 70.0 g |
| talc | 8.5 g |
| calcium stearate | 1.5 g |
| hydroxypropylmethylcellulose | 2.36 g |
| shellac | 0.64 g |
| water | q.s. |
| methylene chloride | q.s. |

The active ingredient, the lactose and 40 g of the corn starch are mixed, and the mixture is moistened with a paste, prepared from 15 g of the corn starch and water (with heating), and granulated. The granules are dried, the remaining corn starch, the talc and the calcium stearate are added and mixed with the granules. The mixture is compressed to form tablets, hich are coated with a solution of the hydroxypropylmethylcellulose and the shellac in methylene chloride; final weight of the film-coated tablet: 580 mg.

FORMULATION EXAMPLE 3

Gelatin dry-filled capsules, containing 500 mg of active ingredient, for example 3-aminopropyl(cyclohexylmethyl)phosphinic acid or a salt, for example the hydrochloride, thereof, can be prepared, for example, as follows:

| Composition (for 1000 capsules) | |
|---|---|
| active ingredient | 500.0 g |
| lactose | 250.0 g |
| microcrystalline cellulose | 30.0 g |
| sodium lauryl sulfate | 2.0 g |
| magnesium stearate | 8.0 g |

The sodium lauryl sulfate is added to the lyophilised active ingredient through a sieve having a mesh size of 0.2 mm. The two components are intimately mixed. Then, first the lactose is added through a sieve having a mesh size of 0.6 mm and then the microcrystalline cellulose through a sieve having a mesh size of 0.9 mm. The mixture is again intimately mixed for 10 minutes. Finally, the magnesium stearate is added through a sieve having a mesh size of 0.8 mm. After further mixing for 3 minutes, gelatin dry-fill capsules of a suitable size are each filled with 790 mg of the resulting formulation.

FORMULATION EXAMPLE 4

A 5% injection or infusion solution of 3-aminopropyl(cyclohexylmethyl)phosphinic acid or of a salt, for example the hydrochloride, thereof can be prepared, for example, as follows:

| Composition (for 1000 or 400 ampoules) | |
|---|---|
| active ingredient | 125.0 g |
| sodium chloride | 22.5 g |
| phosphate buffer pH = 7.4 | 300.0 g |
| demineralised water | ad 2500.0 ml |

The active ingredient and the sodium chloride are dissolved in 1000 ml of water and filtered through a micro-filter. The buffer solution is added, and the mixture is made up to 2500 ml with water. To prepare unit dose forms, 1.0 or 2.5 ml are introduced into each glass ampoule, which then contains 50 or 125 mg, respectively, of active ingredient.

FORMULATION EXAMPLE 5

In a manner analogous to that described in the above Formulation Examples 1 to 4, it is also possible to prepare pharmaceutical compositions comprising a compound according to any one of Preparation Examples 1 to 25 or a compound having $GABA_B$-antagonistic properties that is known per se, for example one of the compounds of formula I proposed according to the invention for use as active ingredients in anti-epileptic medicaments, especially 3-aminopropyl(n-butyl)phosphinic acid,
3-aminopropyl(diethoxymethyl)phosphinic acid,
3-aminopropyl(benzyl)phosphinic acid,
3-aminopropyl(1,1-difluorobutyl)phosphinic acid,
3-amino-2-(p-chlorophenyl)propyl(methyl)phosphinic acid,
3-amino-2-hydroxypropyl(cyclohexylmethyl)phosphinic acid,
3-(p-chlorobenzylamino)-2(R)-hydroxypropyl(benzyl)phosphinic acid,
3-amino-2(S)-hydroxypropyl(cyclohexylmethyl)phosphinic acid,
3-amino-2(S)-hydroxypropyl(benzyl)phosphinic acid,
3-(p-chlorobenzylamino)propyl(diethoxymethyl)phosphinic acid,
3-(p-chlorobenzylamino)-2-hydroxypropyl(n-butyl)phosphinic acid,
3-(3,4-dichlorobenzylamino)-2(S)-hydroxypropyl(benzyl)phosphinic acid,
3-(3,4-dichlorobenzylamino)-2(S)-hydroxypropyl(diethoxymethyl)phosphinic acid, and
3-(p-chlorobenzylamino)propyl(cyclohexylmethyl)phosphinic acid,
or a pharmaceutically acceptable salt thereof.

PHARMACOLOGICAL EXAMPLE 1

Inhibition of "spike and wave" discharges in epileptic rats

Method

The action of $GABA_B$-antagonists was tested on male Wistar rats (300–400 g) of the Strasbourg colony. Animals of the 16th or 17th generation of the strain in which 100% of the test animals exhibit "spike and wave" discharges (epileptic rats) and animals of the 16th or 17th generation of the strain in which 0% of the test animals exhibit "spike and wave" discharges (control strain) were used. The rats received water and food ad libidum, and the light/dark cycle was 12/12 hours. The rats were anaesthetised with pentobarbital (40 mg/kg i.p.) and implanted bilaterally with 4 stainless steel electrodes (two in the frontal cortex and two in the parietal cortex). The rats were used for experiments no sooner than one week after the operation.

The rats, which were freely mobile, were accommodated in a Plexiglass cage (17×17×28 cm) (one rat per cage), and, after a 15-minute period for adaptation to the new surroundings, the EEG was recorded over a period of 20 minutes (reference period). The reference line for the particular test series is thus obtained. A $GABA_B$-antagonist was then administered and the EEG was recorded over a period of from 120 to 180 minutes. The rats were kept under constant observation during this period and prevented from falling asleep by gentle manual contact.

Test arrangement

The test compound was dissolved in 0.9% sodium chloride solution and injected in doses of 50, 100, 200 and 400 mg/kg i.p.. Alternatively, the test compound may be administered in a polyethylene glycol, such as Tween ® 80, (2 drops/10 ml of suspension of the test compound in 0.9% sodium chloride solution; the suspension is homogenised at 40° for 10 minutes by means of ultrasound, injection volume: 2 ml/kg) i.p. or by means of a stomach probe p.o.. Test compounds that are soluble with difficulty are advantageously administered in solution in a mixture of dimethyl sulfoxide (not more than 10% by volume) and 0.9% sodium chloride solution or in 45% aqueous hydroxypropyl-$\beta$-cyclodextrin solution. Each animal is treated with all doses in a randomised sequence. The time between two treatments should be at least 5 days. The mean values ±SEM of the sum total duration of the "spike and wave" discharges of 6 rats over a period of 20 minutes are recorded.

Evaluation of data

The sum total duration of the spike and wave discharges (in seconds) is measured for each 20-minute period of the EEG recording. Comparisons between the treatment and the reference period are carried out by means of non-parametric variance analysis of the groups concerned (Friedman test). The control group and the treated groups are compared by means of the Wilcoxon test only when a significant difference between the two groups is found in the Friedmann test. The dose-dependent decrease in the "spike and wave" discharges is shown in the following tables. The significances of the differences according to Wilcoxon between doses marked by an asteriks and dose 0 corresponds to $p<0,005$.

3-Aminopropyl(diethoxymethyl)phosphinic acid (i.p.):

| PERIODS (min) | DOSES (mg/kg) | | | | |
|---|---|---|---|---|---|
| | 0 | 50 | 100 | 200 | 400 |
| 0-20 | 322 ± 51 | 322 ± 53 | 251 ± 73 | 260 ± 44 | 264 ± 54 |
| 20-40 | 362 ± 58 | 281 ± 58 | 193 ± 65 | 134 ± 22 | 105 ± 37 |
| 40-60 | 393 ± 46 | 133 ± 40* | 66 ± 44* | 57 ± 26* | 47 ± 20* |
| 60-80 | 336 ± 37 | 198 ± 28* | 74 ± 59* | 27 ± 16* | 52 ± 44* |
| 80-100 | 337 ± 38 | 195 ± 32 | 195 ± 38 | 46 ± 21* | 42 ± 28* |
| 100-120 | 377 ± 51 | 182 ± 43 | 127 ± 57 | 43 ± 12* | 22 ± 9* |
| REFERENCE LINE | 419 ± 33 | 377 ± 82 | 462 ± 74 | 452 ± 60 | 511 ± 53 |

3-Aminopropyl(diethoxymethyl)phosphinic acid (p.o.):

| PERIODS (min) | DOSES (mg/kg) | | |
|---|---|---|---|
| | 0 | 300 | 500 |
| 0-20 | 263 ± 36 | 91 ± 31* | 123 ± 58 |
| 20-40 | 391 ± 60 | 182 ± 92 | 20 ± 10* |
| 40-60 | 374 ± 86 | 227 ± 127 | 2 ± 1* |
| 60-80 | 369 ± 58 | 122 ± 67 | 7 ± 5* |
| 80-100 | 364 ± 44 | 85 ± 35* | 0 ± 0* |
| 100-120 | 347 ± 58 | 184 ± 86* | 2 ± 1* |
| 120-140 | 391 ± 60 | 239 ± 132* | 2 ± 2* |
| 140-160 | 364 ± 44 | 234 ± 117* | 1 ± 1* |
| REFERENCE LINE | 386 ± 52 | 356 ± 39 | 372 ± 64 |

3-Aminopropyl(n-butyl)phosphinic acid (i.p.):

| PERIODS (min) | DOSES (mg/kg) | | | | |
|---|---|---|---|---|---|
| | 0 | 50 | 100 | 200 | 400 |
| 0-20 | 321 ± 48 | 219 ± 55 | 213 ± 25 | 192 ± 73 | 49 ± 21* |
| 20-40 | 353 ± 59 | 232 ± 45 | 58 ± 18* | 73 ± 21* | 13 ± 6* |
| 40-60 | 299 ± 30 | 137 ± 34* | 59'18* | 40'19* | 5'2* |
| 60-80 | 327 ± 61 | 151 ± 34* | 76 ± 30* | 47 ± 22* | 2 ± 1* |
| 80-100 | 312 ± 55 | 227 ± 53 | 33 ± 12* | 32 ± 30* | 1 ± 1* |
| 100-120 | 282 ± 39 | 258 ± 39 | 107 ± 40 | 95 ± 45 | 0 ± 0* |
| 120-140 | 197 ± 51 | 226 ± 41 | 135 ± 36 | 42 ± 25 | 2 ± 1* |
| 140-160 | 219 ± 52 | 292 ± 39 | 92 ± 21 | 82 ± 44 | 1 ± 1* |
| 160-180 | 270 ± 44 | 309 ± 32 | 131 ± 29 | 58 ± 21* | 2 ± 1* |
| REFERENCE LINE | 369 ± 60 | 340 ± 60 | 435 ± 48 | 430 ± 58 | 425 ± 74 |

3-Aminopropyl(n-butyl)phosphinic acid (p.o.):

| PERIODS (min) | DOSES (mg/kg) | | |
|---|---|---|---|
| | 0 | 300 | 500 |
| 0-20 | 263 ± 36 | 61 ± 23* | 143 ± 45 |
| 20-40 | 391 ± 60 | 65 ± 42* | 134 ± 38 |
| 40-60 | 374 ± 86 | 108 ± 55 | 98 ± 26* |
| 60-80 | 369 ± 58 | 102 ± 59 | 63 ± 16* |
| 80-100 | 364 ± 44 | 73 ± 42* | 36 ± 19* |
| 100-120 | 347 ± 58 | 44 ± 18* | 23 ± 15* |
| 120-140 | 391 ± 60 | 26 ± 11* | 9 ± 19* |
| 140-160 | 364 ± 44 | 0 ± 0* | 0 ± 0* |
| REFERENCE LINE | 384 ± 52 | 231 ± 30 | 285 ± 53 |

3-Aminopropyl(cyclohexylmethyl)phosphinic acid (i.p.):

| PERIODS (min) | DOSES (mg/kg) | | | | | |
|---|---|---|---|---|---|---|
| | 0 | 25 | 50 | 100 | 200 | 400 |
| 0-20 | 333 ± 39 | 163 ± 19 | 63 ± 20* | 133 ± 37* | 61 ± 18* | 38 ± 23* |
| 20-40 | 385 ± 48 | 45 ± 15* | 17 ± 7* | 15 ± 3* | 3 ± 3* | 0 ± 0* |
| 40-60 | 312 ± 50 | 14 ± 5* | 1 ± 1* | 12 ± 3* | 1 ± 1* | 0 ± 0* |
| 60-80 | 392 ± 51 | 29 ± 8* | 11 ± 5* | 3 ± 2* | 0 ± 0* | 0 ± 0* |
| 80-100 | 392 ± 41 | 41 ± 6* | 0 ± 0* | 32 ± 7* | 2 ± 2* | 0 ± 0* |
| 100-120 | 262 ± 30 | 18 ± 8* | 45 ± 22* | 12 ± 5* | 3 ± 2* | 1 ± 1* |
| REFERENCE LINE | 383 ± 38 | 235 ± 26 | 361 ± 75 | 371 ± 66 | 463 ± 55 | 380 ± 77 |

3-Aminopropyl(cyclohexylmethyl)phosphinic acid (p.o.):

| PERIODS (min) | DOSES (mg/kg) | | |
|---|---|---|---|
| | 0 | 300 | 500 |
| 0-20 | 263 ± 36 | 124 ± 53 | 10 ± 6* |
| 20-40 | 391 ± 60 | 157 ± 78 | 0 ± 0* |
| 40-60 | 374 ± 86 | 162 ± 71 | 0 ± 0* |
| 60-80 | 369 ± 58 | 75 ± 43 | 0 ± 0* |
| 80-100 | 364 ± 44 | 116 ± 77 | 0 ± 0* |
| 100-120 | 347 ± 58 | 21 ± 21* | 0 ± 0* |
| 120-140 | 391 ± 60 | 54 ± 38* | 0 ± 0* |
| 140-160 | 364 ± 44 | 47 ± 34* | 0 ± 0* |
| REFERENCE LINE | 386 ± 52 | 337 ± 37 | 426 ± 74 |

3-Aminopropyl(benzyl)phosphinic acid (i.p.):

| PERIODS | DOSES (mg/kg) |
|---|---|

| (min) | 0 | 50 | 100 | 200 | 400 |
|---|---|---|---|---|---|
| 0-20 | 292 ± 57 | 223 ± 57 | 186 ± 43 | 12 ± 11* | 7 ± 4* |
| 20-40 | 306 ± 82 | 68 ± 30* | 39 ± 26* | 2 ± 1* | 0 ± 0* |
| 40-60 | 268 ± 15 | 114 ± 32* | 39 ± 28* | 1 ± 1* | 0 ± 0* |
| 60-80 | 326 ± 69 | 112 ± 34* | 52 ± 30* | 2 ± 2* | 0 ± 0* |
| 80-100 | 326 ± 73 | 140 ± 43 | 36 ± 13* | 2 ± 1* | 0 ± 0* |
| 100-120 | 232 ± 55 | 162 ± 50 | 27 ± 17* | 0 ± 0* | 0 ± 0* |
| REFERENCE LINE | 343 ± 68 | 393 ± 75 | 318 ± 49 | 307 ± 34 | 415 ± 73 |

3-Amino-2-hydroxypropyl(cyclohexylmethyl)phosphinic acid (i.p.):

| PERIODS (min) | DOSES (mg/kg) | | | | | |
|---|---|---|---|---|---|---|
| | 0 | 25 | 50 | 100 | 200 | 400 |
| 0-20 | 294 ± 37 | 240 ± 67 | 192 ± 50 | 98 ± 43* | 7 ± 7* | 7 ± 5* |
| 20-40 | 227 ± 33 | 78 ± 47* | 82 ± 44* | 41 ± 29* | 0 ± 0* | 0 ± 0* |
| 40-60 | 276 ± 34 | 27 ± 8* | 21 ± 9* | 40 ± 39* | 1 ± 1* | 1 ± 1* |
| 60-80 | 281 ± 40 | 35 ± 20* | 8 ± 3* | 16 ± 16* | 1 ± 1* | 3 ± 3* |
| 80-100 | 299 ± 14 | 6 ± 2* | 15 ± 5 | 16 ± 16* | 0 ± 0* | 5 ± 5* |
| 100-120 | 293 ± 14 | 29 ± 14* | 13 ± 5* | 17 ± 17* | 0 ± 0* | 5 ± 5* |
| REFERENCE LINE | 312 ± 36 | 305 ± 65 | 445 ± 74 | 315 ± 60 | 292 ± 26 | 310 ± 50 |

3-Amino-2-hydroxypropyl(cyclohexylmethyl)phosphinic acid (p.o.):

| PERIODS (min) | DOSES (mg/kg) | | |
|---|---|---|---|
| | 0 | 300 | 500 |
| 0-20 | 263 ± 36 | 176 ± 61 | 105 ± 29* |
| 20-40 | 391 ± 60 | 103 ± 42* | 149 ± 43* |
| 40-60 | 374 ± 86 | 95 ± 33* | 117 ± 26* |
| 60-80 | 369 ± 58 | 73 ± 22* | 104 ± 26* |
| 80-100 | 364 ± 44 | 46 ± 14* | 56 ± 30* |
| 100-120 | 347 ± 58 | 19 ± 12* | 32 ± 12* |
| 120-140 | 391 ± 60 | 73 ± 55* | 40 ± 13* |
| 140-160 | 364 ± 44 | 4 ± 4* | 5 ± 4* |
| REFERENCE LINE | 386 ± 52 | 220 ± 43 | 288 ± 46 |

3-Aminopropyl(cyclopropylmethyl)phosphinic acid (i.p.):

| PERIODS (min) | DOSES (mg/kg) | | | |
|---|---|---|---|---|
| | 0 | 100 | 200 | 400 |
| 0-20 | 332 ± 78 | 292 ± 47 | 338 ± 71 | 199 ± 75 |
| 20-40 | 321 ± 47 | 252 ± 24 | 108 ± 54* | 60 ± 34* |
| 40-60 | 334 ± 62 | 107 ± 18* | 100 ± 72* | 7 ± 4* |
| 60-80 | 358 ± 68 | 185 ± 51* | 19 ± 12* | 5 ± 3* |
| 80-100 | 272 ± 37 | 117 ± 30* | 90 ± 46* | 2 ± 2* |
| 100-120 | 339 ± 37 | 151 ± 40* | 54 ± 27* | 4 ± 1* |
| REFERENCE LINE | 372 ± 64 | 392 ± 77 | 447 ± 66 | 352 ± 12 |

3-Aminopropyl(1,1-difluorobutyl)phosphinic acid (i.p.):

| PERIODS (min) | DOSES (mg/kg) | | |
|---|---|---|---|
| | 0 | 100 | 200 |
| 0-20 | 267 ± 39 | 145 ± 57 | 219 ± 61 |
| 20-40 | 266 ± 38 | 63 ± 27* | 71 ± 33* |
| 40-60 | 273 ± 40 | 56 ± 27* | 47 ± 18* |
| 60-80 | 263 ± 37 | 99 ± 46* | 16 ± 11* |
| 80-100 | 264 ± 35 | 87 ± 47* | 14 ± 13* |
| 100-120 | 308 ± 41 | 36 ± 23* | 18 ± 10* |
| REFERENCE LINE | 307 ± 42 | 304 ± 72 | 297 ± 46 |

3-Aminopropyl(1-hydroxybenzyl)phosphinic acid (i.p.):

| PERIODS (min) | DOSES (mg/kg) | | | |
|---|---|---|---|---|
| | 0 | 100 | 200 | 400 |
| 0-20 | 251 ± 56 | 235 ± 74 | 187 ± 80 | 49 ± 17* |
| 20-40 | 273 ± 60 | 222 ± 55 | 78 ± 40* | 16 ± 6* |
| 40-60 | 306 ± 70 | 88 ± 20* | 44 ± 21* | 1 ± 1* |
| 60-80 | 254 ± 48 | 167 ± 63 | 12 ± 6* | 0 ± 0* |
| 80-100 | 262 ± 54 | 130 ± 48 | 20 ± 10* | 9 ± 4* |
| 100-120 | 280 ± 57 | 95 ± 25* | 15 ± 10 | 7 ± 2* |
| REFERENCE LINE | 306 ± 45 | 320 ± 34 | 298 ± 36 | 248 ± 23 |

3-Amino-2-(S)-hydroxypropyl(cyclohexylmethyl)phosphinic acid (i.p.):

| PERIODS (min) | DOSES (mg/kg) | | |
|---|---|---|---|
| | 0 | 25 | 100 |
| 0-20 | 286 ± 47 | 206 ± 48 | 240 ± 60 |
| 20-40 | 310 ± 64 | 97 ± 19* | 12 ± 5* |
| 40-60 | 342 ± 69 | 49 ± 23* | 6 ± 4* |
| 60-80 | 285 ± 47 | 23 ± 14* | 2 ± 1* |
| 80-100 | 292 ± 54 | 4 ± 3* | 4 ± 3* |
| 100-120 | 301 ± 49 | 9 ± 5* | 3 ± 2* |
| REFERENCE LINE | 341 ± 43 | 402 ± 58 | 548 ± 38 |

-continued 3-(3,4-Dichlorobenzylamino)propyl(diethoxymethyl)phosphinic acid (i.p.):

| PERIODS (min) | DOSES (mg/kg) | | | |
|---|---|---|---|---|
| | 0 | 100 | 200 | 400 |
| 0-20 | 321 ± 50 | 119 ± 49 | 148 ± 65 | 310 ± 73 |
| 20-40 | 292 ± 92 | 151 ± 33 | 166 ± 92 | 45 ± 25* |
| 40-60 | 363 ± 96 | 270 ± 68 | 161 ± 103 | 75 ± 44* |
| 60-80 | 313 ± 45 | 151 ± 27 | 200 ± 112 | 100 ± 71* |
| 80-100 | 326 ± 52 | 261 ± 60 | 183 ± 110 | 58 ± 363 |
| 100-120 | 328 ± 72 | 205 ± 40 | 218 ± 58 | 76 ± 48* |
| REFERENCE LINE | 348 ± 58 | 271 ± 64 | 420 ± 48 | 424 ± 55 |

PHARMACOLOGICAL EXAMPLE 2

Inhibition of the "spike and wave" discharges induced by "grand mal" anti-epileptics in epileptic rats

Method and test arrangement

The method and test arrangement correspond to those of Pharmacological Example 1.

3-Aminopropyl(diethoxymethyl)phosphinic acid: Antagonism of the "spike and wave" discharges induced by carbamazepine. 3-Aminopropyl(diethoxymethyl)phosphinic acid was administered at time 0, and 20 mg/kg of carbamazepine were administered at time 40, in each case i.p..

| PERIODS (min) | DOSES (mg/kg) | | |
|---|---|---|---|
| | 0 | 200 | 400 |
| 0-20 | 289 ± 43 | 353 ± 53 | 115 ± 43 |
| 20-40 | 324 ± 46 | 178 ± 37 | 93 ± 71* |
| 40-60 | 636 ± 43 | 173 ± 78* | 23 ± 14* |
| 60-80 | 669 ± 14 | 70 ± 64* | 29 ± 29* |
| 80-100 | 675 ± 75 | 18 ± 17* | 9 ± 9* |
| REFERENCE LINE | 337 ± 58 | 357 ± 30 | 310 ± 69 |

3-Aminopropyl(diethoxymethyl)phosphinic acid: Antagonism of the "spike and wave" discharges induced by phenytoin. 3-Aminopropyl(diethoxymethyl)phosphinic acid was administered at time 0, and 20 mg/kg of phenytoin were administered at time 40, in each case i.p..

| PERIODS (min) | DOSES (mg/kg) | | |
|---|---|---|---|
| | 0 | 200 | 400 |
| 0-20 | 382 ± 62 | 394 ± 87 | 139 ± 61 |
| 20-40 | 330 ± 58 | 172 ± 64 | 48 ± 40 |
| 40-60 | 555 ± 24 | 124 ± 85* | 31 ± 31* |
| 60-80 | 658 ± 27 | 239 ± 70* | 56 ± 53* |
| 80-100 | 562 ± 76 | 95 ± 37* | 42 ± 39* |
| REFERENCE LINE | 371 ± 23 | 430 ± 61 | 497 ± 68 |

3-Aminopropyl(diethoxymethyl)phosphinic acid: Antagonism of the "spike and wave" discharges induced by Vigabatrin ®. 3-Aminopropyl(diethoxymethyl)phosphinic acid was administered at time 0, and 20 mg/kg of Vigabatrin ® were administered at time 160, in each case i.p..

| PERIODS (min) | DOSES (mg/kg) | | |
|---|---|---|---|
| | 0 | 200 | 400 |
| 240-260 | 875 ± 63 | 213 ± 52* | 44 ± 13* |
| 260-280 | 938 ± 65 | 249 ± 57* | 28 ± 8* |
| REFERENCE LINE | 408 ± 68 | 310 ± 34 | 363 ± 44 |

What is claimed is:

1. An araliphatically N-substituted aminoalkanephosphinic acid of formula I

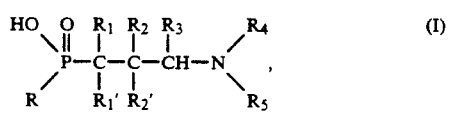

wherein $R_1$, $R_1'$, $R_2$, $R_2'$ and $R_3$ are hydrogen, $R_4$ is a phenyl-lower alkyl or naphthyl-lower alkyl each of which is unsubstituted or mono-, di- or tri-substituted by lower alkyl, lower alkoxy, halogen and/or by trifluoromethyl other than unsubstituted 1-phenyl-lower alkyl, $R_5$ is hydrogen or lower alkyl, and R is lower alkyl having at least 2 carbon atoms, lower alkenyl, lower alkynyl, oxo-lower alkyl, hydroxy- or dihydroxy-lower alkyl, hydroxy-lower alkenyl, mono-, di- or poly-halo-lower alkyl, mono-, di- or poly-halo-lower alkenyl, mono-, di- or poly-halo(hydroxy)-lower alkyl, mono-, di- or poly-halo(hydroxy)-lower alkenyl, lower alkoxy-lower alkyl, di-lower alkoxy-lower alkyl, lower alkoxy(hydroxy)-lower alkyl, lower alkoxy(halo)-lower alkyl, lower alkylthio-lower alkyl, di-lower alkylthio-lower alkyl, cycloalkyl, hydroxycycloalkyl, cycloalkyl-lower alkyl, cycloalkenyl-lower alkyl, cycloalkyl(hydroxy)-lower alkyl, (lower alkylthio)cycloalkyl(hydroxy)-lower alkyl or phenyl-lower alkyl or naphthyl-lower alkyl each of which is unsubstituted or mono- or di-substituted by lower alkyl, lower alkoxy, halogen and/or by trifluoromethyl, or a pharmaceutically acceptable salt thereof.

2. A compound as claimed in claim 1, of formula I, wherein $R_1$, $R_1'$, $R_2$, $R_2'$ and $R_3$ are hydrogen, $R_4$ is a phenyl- or naphthyl-lower alkyl radical each of which is unsubstituted or mono-, di- or tri-substituted in the phenyl or naphthyl moiety by lower alkyl, lower alkoxy and/or by halogen, $R_5$ is hydrogen or lower alkyl, and R is lower alkyl having at least 2 carbon atoms, lower alkenyl, lower alkynyl, oxo-lower alkyl, hydroxy- or dihydroxy-lower alkyl, hydroxy-lower alkenyl, mono-, di- or poly-halo-lower alkyl, mono-, di- or poly-halo-lower alkenyl, mono-, di- or poly-halo(hydroxy)-lower alkyl, mono-, di- or poly-halo(hydroxy)-lower alkenyl, lower alkoxy-lower alkyl, di-lower alkoxy-lower alkyl, lower alkoxy(hydroxy)-lower alkyl, lower alkoxy(halo)-lower alkyl, lower alkylthio-lower alkyl, di-lower alkylthio-lower alkyl, cycloalkyl, hydroxycycloalkyl, cycloalkyl-lower alkyl, cycloalkenyl-lower alkyl, cycloalkyl(hydroxy)-lower alkyl, (lower alkylthio)cycloalkyl(hydroxy)-lower alkyl, or phenyl-lower alkyl or naphthyl-lower alkyl each of which is unsubstituted or mono- or di-substituted by lower alkyl, lower alkoxy, halogen and/or trifluoromethyl, or a pharmaceutically acceptable salt thereof.

3. A compound as claimed in claim 1, of formula I, wherein $R_1$, $R_1'$, $R_2$, $R_2'$ and $R_3$ are hydrogen, $R_4$ is a phenyl- or naphthyl-lower alkyl radical each of which is unsubstituted or substituted by lower alkyl, lower alkoxy and/or by halogen, $R_5$ is hydrogen or lower alkyl, and R is lower alkyl having at least 2 carbon atoms, lower alkenyl, lower alkynyl, oxo-lower alkyl, hydroxy- or dihydroxy-lower alkyl, hydroxy-lower alkenyl, mono-, di- or poly-halo-lower alkyl, mono-, di- or poly-halo-lower alkenyl, mono-, di- or poly-halo(hydroxy)-lower alkyl, mono-, di- or poly-halo(hydroxy)-lower alkenyl, lower alkoxy-lower alkyl, di-lower alkoxy-lower alkyl, lower alkoxy(hydroxy)-lower alkyl, lower alkoxy(halo)-lower alkyl, lower alkylthio-lower alkyl, di-lower alkylthio-lower alkyl, cycloalkyl, hydroxycycloalkyl, cycloalkyl(hydroxy)-lower alkyl and (lower alkylthio)cycloalkyl(hydroxy)-lower alkyl, or phenyl-lower alkyl or naphthyl-lower alkyl each of which is unsubstituted or mono- or di-substituted by lower alkyl, lower alkoxy, halogen and/or by trifluoromethyl, or a pharmaceutically acceptable salt thereof.

4. A compound as claimed in claim 1, of formula I, wherein R is $C_3$–$C_7$alkyl, $\alpha,\alpha,$di-$C_1$–$C_4$alkoxy-$C_1$–$C_4$alkyl, $C_3$–$C_6$cycloalkyl-$C_1$–$C_4$alkyl, $C_3$–$C_6$cycloalkenyl-$C_1$–$C_4$alkyl or benzyl that is unsubstituted or mono-, di- or tri-substituted by $C_1$–$C_4$alkyl, $C_1$–$C_4$alkoxy and/or by halogen, $R_1$, $R_1'$, $R_2$, $R_2'$ and $R_3$ are hydrogen, $R_4$ is phenyl-$C_1$–$C_4$alkyl is unsubstituted or mono-, di- or tri-substituted by $C_1$–$C_4$alkyl, $C_1$–$C_4$alkoxy and/or by halogen, or is naphthyl-$C_1$–$C_4$alkyl that is unsubstituted or monosubstituted by halogen having an atomic number of up to and including 35, and $R_5$ is hydrogen or $C_1$–$C_4$alkyl, or a pharmaceutically acceptable salt thereof.

5. A compound as claimed in claim 1, of formula I, wherein $R_1$, $R_1'$, $R_2$, $R_2'$ and $R_3$ are hydrogen, $R_2$ is hydrogen or hydroxy, $R_4$ is phenyl-$C_1$–$C_4$alkyl that is unsubstituted or mono- or di-substituted by halogen having an atomic number of up to and including 35, $R_5$ is hydrogen or $C_1$–$C_4$alkyl, and R is $C_3$–$C_5$alkyl, $\alpha,\alpha$-di-$C_1$–$C_4$alkoxymethyl, $C_3$–$C_6$cycloalkyl-$C_1$–$C_4$alkyl or benzyl, or a pharmaceutically acceptable salt thereof.

6. A compound as claimed in claim 1 being
3-(p-chlorobenzylamino)propyl(diethoxymethyl)-phosphinic acid,
3-(p-chlorobenzylamino)propyl(n-butyl)phosphinic acid,
3-(p-chlorobenzylamino)propyl(cyclohexylmethyl)-phosphinic acid,
3-(3,4-dichlorobenzylamino)propyl(diethoxymethyl)-phosphinic acid,
3-[1-(p-chlorophenyl)ethylamino]propyl(diethoxymethyl)phosphinic acid,
3-(naphth-1-ylmethylamino)propyl(diethoxymethyl)-phosphinic acid,
3-(3,4-dichlorobenzylamino)propyl(cyclohexylmethyl)phosphinic acid,
3-(p-fluorobenzylamino)propyl(diethoxymethyl)-phosphinic acid,
3-(4-chloro-3-trifluoromethylbenzylamino)propyl(-diethoxymethyl)phosphinic acid,
3-(m-chlorobenzylamino)propyl(diethoxymethyl)-phosphinic acid,
3-[1-(3,4-dichlorophenyl)ethylamino]propyl(diethoxymethyl)phosphinic acid,
3-(p-iodobenzylamino)propyl(diethoxymethyl)phosphinic acid,
3-(2,4-dichlorobenzylamino)propyl(diethoxymethyl)-phosphinic acid,
3-(o-chlorobenzylamino)propyl(diethoxymethyl)-phosphinic acid,
3-(3,4-dichlorobenzylamino)propyl(cyclopropylmethyl)phosphinic acid,
3-[N-(p-chlorobenzyl)-N-methylamino]propyl(diethoxymethyl)phosphinic acid,
3-[2-(p-chlorophenyl)prop-2-ylamino]propyl(diethoxymethyl)phosphinic acid,
3-[2-(3,4-dichlorophenyl)prop-2-ylamino]propyl(diethoxymethyl)phosphinic acid,
3-[2-(3,4-dichlorophenyl)prop-2-ylamino]-2(S)-hydroxypropyl(benzyl)phosphinic acid,
3-(4-chloro-3-methoxy-benzylamino)propyl(diethoxymethyl)phosphinic acid,
3-(3-chloro-4-methoxy-benzylamino)-2(S)-hydroxypropyl(benzyl)phosphinic acid,
3-(2-phenylethylamino)propyl(diethoxymethyl)phosphinic acid,
3-(3,4-dichloro-6-iodo-benzylamino)propyl(diethoxymethyl)phosphinic acid,
3-(4-chloro-3-iodo-benzylamino)propyl(diethoxymethyl)phosphinic acid,
3-(3-chloro-4-iodo-benzylamino)propyl(diethoxymethyl)phosphinic acid,
3-Di(p-chlorobenzyl)aminopropyl(diethoxymethyl)-phosphinic acid, or a pharmaceutically acceptable salt thereof.

7. A pharmaceutical composition comprising a therapeutically effective amount of a compound of formula I

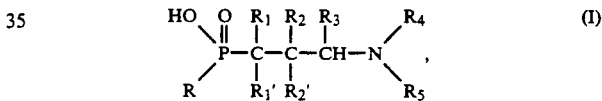

wherein $R_1$, $R_1'$, $R_2$, $R_2'$ and $R_3$ are hydrogen, $R_4$ is a phenyl-lower alkyl or naphthyl-lower alkyl each of which is unsubstituted or mono-, di- or tri-substituted by lower alkyl, lower alkoxy, halogen and/or by trifluoromethyl, $R_5$ is hydrogen or lower alkyl, and R is lower alkyl having at least 2 carbon atoms, lower alkenyl, lower alkynyl, oxo-lower alkyl, hydroxy- or dihydroxy-lower alkyl, hydroxy-lower alkenyl, mono-, di- or poly-halo-lower alkyl, mono-, di- or poly-halo-lower alkenyl, mono-, di- or poly-halo(hydroxy)-lower alkyl, mono-, di- or poly-halo(hydroxy)-lower alkenyl, lower alkoxy-lower alkyl, di-lower alkoxy-lower alkyl, lower alkoxy(hydroxy)-lower alkyl, lower alkoxy(halo)-lower alkyl, lower alkylthio-lower alkyl, di-lower alkylthio-lower alkyl, cycloalkyl, hydroxycycloalkyl, cycloalkyl-lower alkyl, cycloalkenyl-lower alkyl, cycloalkyl(hydroxy)-lower alkyl, (lower alkylthio)cycloalkyl(hydroxy)-lower alkyl or phenyl-lower alkyl or naphthyl-lower alkyl each of which is unsubstituted or mono- or di-substituted by lower alkyl, lower alkoxy, halogen and/or by trifluoromethyl, in free form or in the form of a pharmaceutically acceptable salt, together with customary pharmaceutical excipients.

8. A pharmaceutical composition according to claim 7 comprising, as the active ingredient, a therapeutically effective amount of a compound of formula I or a pharmaceutically acceptable salt thereof.

9. A pharmaceutical composition according to claim 7 for the treatment of epilepsies of the "petit mal" type and for suppressing "petit mal"-type conditions which may arise in the case of treatment with known anti-epileptics, which composition comprises as active ingredient a therapeutically effective amount of at least one compound of formula I having $GABA_B$-antagonistic properties.

10. A pharmaceutical composition according to claim 9 in unit dose form.

11. A pharmaceutical composition according to claim 9 in an enteral unit dose form.

12. A composition of claim 9 in the form of a tablet, film-coated tablet, gelatin capsule, dry-filled capsule or dragée.

13. A pharmaceutical composition according to claim 9 in a dosage form suitable for parenteral administration.

14. A pharmaceutical composition according to claim 9 in the form of an injection or infusion solution.

15. A pharmaceutical composition according to claim 9 comprising from approximately 30 to approximately 600 mg of said active ingredient per unit dose.

16. A pharmaceutical composition according to claim 9 comprising from approximately 100 to approximately 200 mg of said active ingredient per unit dose.

17. An injection or infusion solution according to claim 14 comprising from approximately 1 to approximately 10% by weight of said active ingredient.

18. A pharmaceutical composition according to claim 9 containing 3-[1-(3,4-dichlorophenyl)ethylamino]-propyl(diethoxymethyl)phosphinic acid or a pharmaceutically acceptable salt thereof.

19. A method for the treatment of an epilepsy of the "petit mal" type and for suppressing "petit mal"-type conditions which may arise in the case of treatment with known anti-epileptics and of symptoms of cerebral insufficiencies, emotional depression and anxiety conditions, which comprises an effective amount of a compound according to claim one having $GABA_B$-antagonistic properties is administered to a warm-blooded organism in need of such treatment.

20. A method of treatment according to claim 19 comprising administering a therapeutically effective amount of 3-[1-(3,4-dichlorophenyl)ethylamino]-propyl(diethoxymethyl)phosphinic acid or a pharmaceutically acceptable salt thereof to a warm blooded animal in need thereof.

* * * * *

UNITED STATES PATENT AND TRADEMARK OFFICE
CERTIFICATE OF CORRECTION

PATENT NO. : 5,229,379

DATED : July 20, 1993

INVENTOR(S) : MARESCAUX ET AL

It is certified that error appears in the above-identified patent and that said Letters Patent is hereby corrected as shown below:

Column 39:

In claim 5, lines 2-3, delete "$R_2$ is hydrogen or hydroxy,"

Signed and Sealed this

Fifth Day of April, 1994

BRUCE LEHMAN

Attest:

Attesting Officer

Commissioner of Patents and Trademarks